United States Patent [19]
Chenchik et al.

[11] Patent Number: 5,962,272
[45] Date of Patent: *Oct. 5, 1999

[54] METHODS AND COMPOSITIONS FOR FULL-LENGTH CDNA CLONING USING A TEMPLATE-SWITCHING OLIGONUCLEOTIDE

[75] Inventors: Alex Chenchik, Palo Alto; York Zhu, Sunnyvale; Luda Diatchenko, Palo Alto; Paul Siebert, Sunnyvale, all of Calif.

[73] Assignee: Clontech Laboratories, Inc., Palo Alto, Calif.

[*] Notice: This patent is subject to a terminal disclaimer.

[21] Appl. No.: 08/778,494

[22] Filed: Jan. 3, 1997

Related U.S. Application Data

[63] Continuation-in-part of application No. 08/582,562, Jan. 3, 1996.

[51] Int. Cl.[6] ............................ C12P 19/34; C07H 21/04; C07H 21/02
[52] U.S. Cl. .................... 435/91.1; 435/91.2; 536/23.1; 536/24.2; 536/25.3
[58] Field of Search ................................ 435/91.1, 91.2, 435/810; 536/23.1, 24.2, 25.3

[56] References Cited

U.S. PATENT DOCUMENTS

| | | | |
|---|---|---|---|
| 3,850,749 | 11/1974 | Kaufmann et al. | 195/28 N |
| 5,219,989 | 6/1993 | Sonenberg | 530/350 |
| 5,436,149 | 7/1995 | Barnes | 435/194 |

(List continued on next page.)

FOREIGN PATENT DOCUMENTS

| | | |
|---|---|---|
| 0346877 | 12/1989 | European Pat. Off. . |
| 0490281 | 12/1991 | European Pat. Off. . |
| 0625572 | 11/1994 | European Pat. Off. . |

(List continued on next page.)

OTHER PUBLICATIONS

Carninci et al., Genomics 37, 327–336 (1996).
Zhu et al., FASEB J. 10(6), A1126 (Abstract; Apr. 1996).
CLONTECH 1996/1997 Catalog, pp. 54–55.
CLONTECHniques, vol. XI, No. 1, Jan. 1996.
Wu, R. ed. (1987) *Methods in Enzymology*, vol. 152, Academic Press, pp. 307–389.
Gubler, U., B.J. Hoffman (1983) *Gene* 25:253–269.
Okayma and Berg (1982) *Mol. Cell. Biol.* 2:161–170.

(List continued on next page.)

*Primary Examiner*—Kenneth R. Horlick
*Attorney, Agent, or Firm*—Benjamin Aaron Adler

[57] ABSTRACT

The present invention pertains to methods for the synthesis and cloning of full-length cDNA, or cDNA fragments, that correspond to the complete sequence of 5'-ends of mRNA molecules. The method of the present invention comprises contacting RNA with a cDNA synthesis primer which can anneal to RNA, a suitable enzyme which possesses reverse transcriptase activity, and a template switching oligonucleotide under conditions sufficient to permit the template-dependent extension of the primer to generate an mRNA-cDNA hybrid. The template switching oligonucleotide hybridizes to the CAP site at the 5'-end of the RNA molecule and serves as a short, extended template for CAP-dependent extension of the 3'-end of the ss cDNA that is complementary to the template switching oligonucleotide. The resulting full-length ss cDNA includes the complete 5'-end of the RNA molecule as well as the sequence complementary to the template switching oligonucleotide, which can then serve as a universal priming site in subsequent amplification of the cDNA.

The subject invention also pertains to the template switching oligonucleotides that can be used according to the subject method. Kits containing the template switching oligonucleotide are also included within the scope of the present invention.

29 Claims, 6 Drawing Sheets

U.S. PATENT DOCUMENTS

| | | | |
|---|---|---|---|
| 5,597,713 | 1/1997 | Kato et al. | 435/91.41 |
| 5,659,025 | 8/1997 | Engels et al. | 536/23.1 |
| 5,668,269 | 9/1997 | Engels et al. | 536/25.32 |
| 5,750,673 | 5/1998 | Martin | 536/26.1 |

FOREIGN PATENT DOCUMENTS

| | | |
|---|---|---|
| 9011369 | 10/1990 | WIPO . |
| 9117755 | 11/1991 | WIPO . |

OTHER PUBLICATIONS

Edery, A., L.L. Chu, N. Sonenberg, J. Pelletier (1995) *Mol. Cell. Biol.* 15:3363–3371.

Maruyama, K., S. Sugano (1994) *Gene* 138:171–174.

Fromomt–Racine, M., E.B. Pictet, T. Grande (1993) *Nucl. Acids Res.* 21:1683–1684.

Kato, S. (1994) *Gene* 150:243–250.

Kimmel, A.R., S.L. Berger (1987) "Preparation of cDNA and the generation of cDNA libraries: Overview," *Meth. Enzymol.* 152:307–316.

Bertling, W.M., F. Beier, and E. Reichenberger (1993) "Determination of 5' Ends of Specific mRNAs by DNA Ligase–dependent Amplification," *PCR Methods and Applications*, Oct., No. 2, New York, NY, pp. 95–99.

Chenchik, A., F. Mogadam, and P. Siebert (1995) "Full–length cDNA amplification using marathon RACE technique," *Faseb J.*, vol. 9, No. 6.

Jean Baptiste Dumas Milne Edwards et al. (1991) "Oligodeoxyribonucleotide ligation to single–stranded cDNAs: a new tool for cloning 5' ends of mRNAs and for constructing cDNA libraries by in vitro amplification," *Nucleic Acids Research*, Oct., vol. 19, No. 19, pp. 5227–5232.

A. B. Troutt et al. (1992) "Ligation–anchored PCR: A simple amplification technique with single–sided specificity," *Proc. Natl. Acad. Sci. USA*, vol. 89, pp. 9823–9825.

Y. Zhu et al. (1996) "CAPswitch based PCR technology for full–length cDNA library construction from small amount of RNA," *Faseb J.*, vol. 10, No. 6.

METHODS AND COMPOSITIONS FOR FULL-LENGTH CDNA CLONING USING A TEMPLATE-SWITCHING OLIGONUCLEOTIDE

CROSS REFERENCE TO A RELATED APPLICATION

This application is a continuation-in-part of U.S. application Ser. No. 08/582,562, filed Jan. 3, 1996.

FIELD OF THE INVENTION

The present invention relates to improved technology for selectively synthesizing full-length cDNA having complete sequence information of full-length mRNA.

BACKGROUND OF THE INVENTION

A basic technology in the field of molecular biology is the conversion of poly(A)+RNA (mRNA) to double-stranded (ds) complementary DNA (cDNA), which then can be inserted into a cloning vector for generating a cDNA library or expression in an appropriate host cell. Advances in cDNA library construction technology have made possible the discovery and production of a wide range of biologically important proteins.

Several procedures for generating cDNA libraries which have been used during the last 15 years are comprehensively reviewed in Wu, ed. *Methods in Enzymology* (1987), vol. 152. For the most part, cDNA library construction technologies use poly(A)+RNA as a starting material. The intact poly(A)+RNA is characterized by a polyadenylated "tail" at its 3' end and a characteristic "CAP structure or cap site" at the 5' end. A critical requirement for cDNA library construction is to completely copy poly(A)+RNA to full-length cDNA and retain the complete sequence information on the structure of the protein encoded by mRNA.

One generalized and commonly used method by which the poly(A)+RNA is copied into cDNA employs reverse transcriptase, which starts at the 3' end of the mRNA from an oligo d(T) primer and proceeds towards the 5' end to generate a cDNA:mRNA hybrid (Gubler et al., 1983). The RNA strand is then removed from the hybrid by action of RNase H and a second DNA strand is then synthesized using DNA polymerase I. The resulting heterogeneous mixture of ds cDNA molecules can then be cloned into suitable recombinant DNA vector molecules using a variety of techniques. Unfortunately, for the majority of mRNAs, this method does not allow for the synthesis of "full-length" cDNA because reverse transcriptase can not efficiently copy them into full-length cDNAs. The efficiency of copying is inversely proportional to the length of mRNA; thus, the problem of "full-length" cDNA synthesis is more acute for longer mRNAs. Moreover, the current technology can generate deletions at the 5' and 3' ends of the cDNA.

In an alternative approach, poly(A) tails of mRNA molecules are first annealed to oligo (dT) linking with linearized vector DNA (vector primer)(Okayama et al., 1982; Pruitt, International Patent, Appl. No. 89110816.9). Then, the first strand of cDNA synthesized by reverse transcriptase is tailed at the 3' end by oligo dt which facilitates subsequent cloning by circularization into vector primer. This method also generates greater numbers of cDNA clones that contain truncated cDNAs due to non-full-length cDNA synthesis.

As a result of the shortcomings using present technologies to generate conventional cDNA libraries, the majority of the cDNA clones lack sequences close to the 5' end of the mRNAs. This results in a loss of important information required to make functional proteins. Two selection procedures have been developed in efforts to enrich cDNA libraries for "full-length" cDNA clones. In CAP retention procedure (CAPture) cap-binding protein (eukaryotic initiation factor 4E) in combination with RNase A was used to purify full-length cDNA:mRNA hybrids (Edery et al., 1995; Sonenberg et al., U.S. Pat. No. 5,219,989). Shorter duplexes corresponding to non-full-length cDNA fragments are not selected, since the CAP structure of mRNA is removed from the RNA moiety by nuclease treatment. Although the CAPture method could potentially enrich cDNA libraries for clones containing the authentic 5' ends, the yield of full-length cDNA is very low, especially for long cDNAs (1–5%). The low yield is a significant disadvantage for this technology.

In the "oligo-capping" method, the CAP structure of mRNA is selectively replaced with an oligoribonucleotide, thus generating chimeric oligonucleotide/full-length mRNA intermediates which are subsequently used for synthesis of full-length cDNAs (Maruyama et al., 1994; Fromomt-Racine et al., 1993; Kato et al., International Patent, Publ. No. 0 625 572 A1, Appl. No. 93921061.3). However, this method is complicated, involving treatment of mRNA with an alkaline phosphatase, decapping mRNA with tobacco acid pyrophosphatase, and ligation of the oligonucleotide to the 5' end of mRNA by T4 RNA ligase. These multiple enzymatic steps degrade mRNA, thereby generating incomplete cDNA fragments for subsequent cloning procedures. Size distribution of cDNA inserts in cDNA libraries generated using the "oligo-capping" method is typically less than 3 kb. This is much less than full-length mRNA size distribution (Kato et al., 1994) and indicates the low efficiency of "full-length" cDNA cloning by "oligo-capping" technology.

As can be understood from the foregoing, conventional methods for constructing cDNA libraries containing full-length cDNA clones are restricted by low efficiency and the use of multiple, time-consuming steps. Accordingly, a simple method that would generate high quality, full-length cDNA from RNA is highly desirable.

BRIEF SUMMARY OF THE INVENTION

The present invention provides an advantageous method for synthesis and cloning of full-length cDNA, or cDNA fragments, that corresponds to the complete sequence of 5'-ends of mRNA molecules. The method of the present invention comprises contacting RNA with a cDNA synthesis primer which can anneal to RNA, a suitable enzyme which possesses reverse transcriptase activity, and a template switching oligonucleotide under conditions sufficient to permit the template-dependent extension of the primer to generate an mRNA-cDNA hybrid. The resulting full-length ss cDNA includes the complete 5'-end of the RNA molecule as well as the sequence complementary to the template switching oligonucleotide, which can then serve as a universal priming site in subsequent amplification of the cDNA.

The subject invention also concerns novel template switching oligonucleotides that can be used according to the subject method. Kits containing the template switching oligonucleotide are also included within the scope of the present invention.

DETAILED DISCLOSURE OF THE INVENTION

Figure 1:
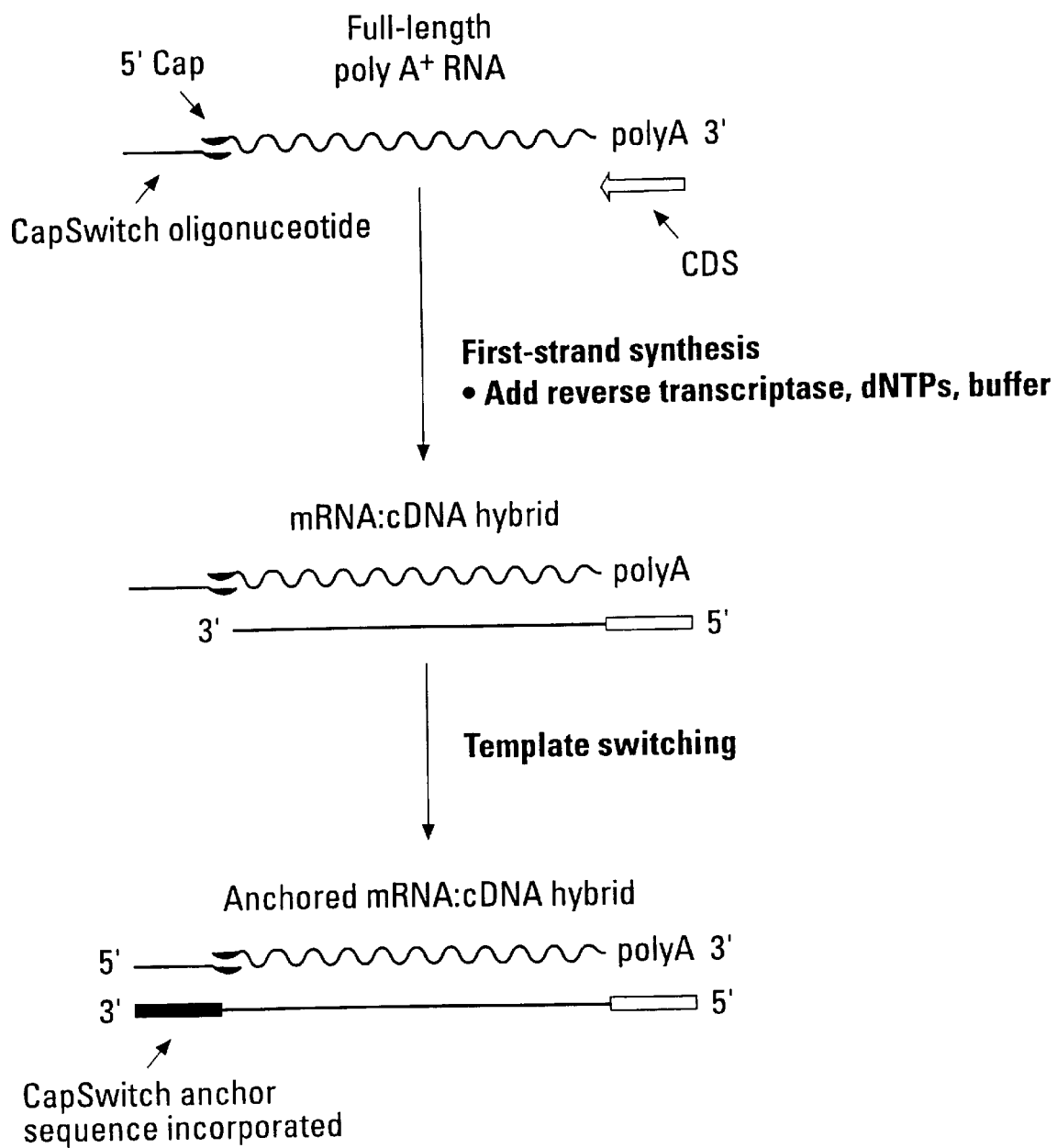
FIG. 1 shows a representation of a mechanism of template switching technology according to the subject invention.

The subject invention concerns compositions and methods for constructing cDNA libraries from nanogram quantities of total or poly A+ RNA. The compositions and methods employ template switching oligonucleotides described herein. The method of the present invention comprises contacting RNA with a primer which can anneal to RNA, a reverse transcriptase, and a template switching oligonucleotide under conditions sufficient to permit the template-dependent extension of the annealed primer to generate an mRNA-cDNA hybrid. The resulting full-length ss cDNA includes the complete 5'-end of the RNA molecule, as well as the sequence complementary to the template switching oligonucleotide. The template switching complementary sequence can then serve as a universal priming site in subsequent amplification of the cDNA.

Specifically, the subject invention provides a method for synthesis of full-length single-stranded (ss) cDNA, or ss cDNA fragments, from RNA. The cDNA synthesized in the present method has an arbitrary anchor sequence at the 3' end, followed by a nucleotide sequence complementary to the RNA molecule starting from the cap site of the mRNA. In a preferred embodiment, the process of the subject invention comprises the following steps:

1. Incubating a sample of poly(A)+RNA or total RNA in the presence of a cDNA synthesis primer (CDS primer) which can anneal to mRNA and an enzyme which possesses reverse transcriptase activity under conditions sufficient to permit the template-dependent extension of the primer to generate an mRNA-cDNA hybrid; and 2. incubating the first-strand cDNA synthesis mixture obtained from step 1 with a template switching oligonucleotide of the present invention (also referred to herein as a "CAPswitch oligonucleotide"), which can provide CAP-dependent extension of full-length cDNA by reverse transcriptase using the template switching oligonucleotide as a template, and thereby adding nucleotide sequence complementary to the template switching oligonucleotide to the 3'-end of full-length ss cDNA (referred to herein as "anchored cDNA:mRNA hybrid"). The template switching oligonucleotide has a pre-selected arbitrary nucleotide sequence at its 5'-end and at least one riboguanine residue at its 3'-end.

Steps 1 and 2 of the method are separated only in time. In a preferred embodiment, step 1 is followed by step 2. However, it would be understood that the first-strand cDNA synthesis mixture from step 1 can include a template switching oligonucleotide which will be used at step 2. Alternatively, a template switching oligonucleotide can be added to the reaction mixture at the time of or after first-strand cDNA synthesis. In a preferred embodiment, the cDNA synthesis primer is a modified oligo(dT) primer.

The scope of the present invention also includes a method for isolating a full-length cDNA fragment corresponding to a 5'-end of target mRNA(s) using anchored cDNA:mRNA hybrid generated at step 2 as a template. This method comprises the embodiment of steps 1 and 2, followed by either alternative step 3A or step 3B, described below:

3A. Incubating an anchored cDNA:mRNA hybrid generated at step 2 with a combination of (a) an oligonucleotide primer corresponding partially or completely to the nucleotide sequence of the template switching oligonucleotide, (b) oligonucleotide primer(s) which is complementary to a nucleotide sequence of the target (s) mRNA, and (c) an effective amount of other reagents necessary to perform polymerase chain reaction (PCR). The incubation is conducted under conditions sufficient to perform PCR and thereby generate amplification product corresponding to the 5'-end full-length fragment of target cDNA.

3B. Treating anchored cDNA:mRNA hybrid of step 2 under conditions in which a second cDNA strand is synthesized, using the first anchored cDNA strand as a template.

Also within the scope of the present invention is a method for generating cDNA libraries containing full-length cDNAs. This method uses as a template anchored cDNA:mRNA hybrid generated at step 2. This method comprises the embodiment of steps 1 and 2, followed by either alternative step 3C or step 3D, described below:

3C. Incubating anchored cDNA:mRNA hybrid generated at step 2 with a combination of primers corresponding partially or completely to the sequence of template switching oligonucleotide and cDNA synthesis primer, respectively, and an effective amount of other reagents necessary to perform PCR. The incubation is conducted under conditions sufficient to perform PCR to generate amplification product corresponding to the representative library of full-length ds cDNA.

3D. Treating anchored cDNA mRNA hybrid of step 2 under conditions in which a second cDNA strand is synthesized, using the first anchored cDNA strand as a template.

In one aspect of the present invention, the resulting cDNA product generated at step 2 or 3 can be inserted into recombinant cloning vehicles, and hosts can be transformed with these vehicles according to conventional methods well known in art (Kimmel et al., 1987).

The subject invention enables synthesis of full-length cDNA, which has been difficult to synthesize by conventional methods. The present invention includes the novel step 2 described above, which can be utilized in standard cDNA preparation/cloning procedures which are well known in the art. The use of template switching oligonucleotides in the subject method advantagously allows for negative selection against cDNAs that are not complementary with the 5'-end of template RNA, whereas full-length cDNAs can be readily selected. Moreover, the subject methods can significantly simplify cDNA synthesis and cloning. Since the cDNA clones obtained from the full-length cDNA library prepared according to the present method contain the complete information for the primary structure of the protein, the invention also relates to a process for using the clones, obtained from said full-length cDNA library to produce the encoded proteins.

In another aspect, the invention provides methods where the resulting cDNA product generated at step 3 can be used as a starting material for use with cDNA subtraction methods. Specifically, the method of the subject invention can be used in conjunction with cDNA subtraction procdures to prepare a cDNA population containing highly enriched representation of cDNA species that are present in one DNA population (the tester population), but that are less abundant or absent in another DNA population (the driver population). Preferably, tester and driver ds cDNA amplified by methods and materials of the present invention is used in combination with Suppression Subtractive Hybridization technology described by Chenchik et al. (U.S. Pat. No. 5,565,340). Other methods of subtractive hybridization, described for example, by Wigler et al. (U.S. Pat. No. 5,436,142); Hampson et al. (Nucl. Acids Res. 20:2899 (1992)); Yang et al. (Anal. Biochem. 237:109–114(1996)); Balzer et al. (Nucl. Acids Res. 22:2853–2854(1994)), and others, can also be employed.

The ds cDNA prepared according to the present invention can also be used as a hybridization probe. As used herein, the term "hybridization probe" means that cDNA generated from total RNA isolated from healthy, diseased or infected organisms, or as subtracted as described by Chenchik et al. (U.S. Pat. No. 5,565,340), may be labeled by radioisotopes, fluorescent and other reporter groups by conventional chemical or enzymatic labeling procedures. Labeled cDNA can then be used in standard hybridization assays known in the art, i.e., the labeled cDNA is contacted with the defined oligonucleotide/polynucleotides corresponding to a particular set of the genes immobilized on a solid surface for a sufficient time to permit the formation of patterns of hybridization on the surfaces caused by hybridization between certain polynucleotide sequences in the hybridization probe with the certain immobilized defined oligonucleotide/polynucleotides. The hybridization patterns using available conventional techniques, such as scintillation counting, autoradiography, fluorescence measurement, calorimetric measurement, or light emission measurement. Techniques and conditions for labeling, hybridization and detection are well known in the art (see, e.g. Maniatis et al., 1989; Keller et al., 1993).

Labeled cDNA can also be used for identifying genes which are differentially expressed in two different predetermined states of an organism (see, e.g., Maniatis et al., 1989; International Patent WO 95/21944).

The ss cDNA generated after the first-strand cDNA synthesis-template switching procedure (step 2) or the ds cDNA generated after 5'-RACE amplification step (step 3) can be used as a hybridization probe for selectively recovering a desired complementary target nucleic acid molecule from a mixture or library of ss or ds nucleic acid containing said molecule. The method wherein the hybridization probe is haptenylated and used for obtaining an enriched source of target nucleic acid molecule based on hybridization approach as described in details in U.S. Pat. No. 5,484,702 of Jan. 16, 1996 and U.S. Pat. No. 5,500,356 of Mar. 19, 1996 or RecA protein-mediated hybridization as described in details in U.S. Pat. No. 4,888,274 of Dec. 19, 1989.

Also within the scope of the present invention are template switching or "CAPswitch" oligonucleotides useful for the preparation of cDNA libraries containing full-length cDNA clones. The CAPswitch oligonucleotides have at least two functions. One function is the ability to selectively interact with full-length intermediates of reverse transcriptase-mRNA-cDNA which are generated at the 5' end of full-length mRNA after first-strand cDNA synthesis. A second function of the CAPswitch oligonucleotides of the subject invention is as an efficient template for reverse transcriptase from the above-mentioned full-length intermediates which can allow 5' mRNA end (in most cases CAP-dependent) extension of full-length cDNA by reverse transcriptase using CAPswitch oligonucleotide as a template. A sequence complementary to CAPswitch oligonucleotide can thereby be added to the 3'-end of full-length cDNA.

Also within the scope of the present invention are modifications in the structure or sequence of CAPswitch oligonucleotide which can provide an advantage for selective binding to the CAP structure of mRNA. One modification, for example, can include covalently binding CAPswitch oligonucleotides with a protein capable of binding the CAP structure of mRNA (see U.S. Pat. No. 5,219,984).

The invention particularly concerns the embodiments of the above methods wherein the CAPswitch oligonucleotide is represented by the following formula:

$$5'\text{-}dN_1\text{-}dN_2\text{-} \ldots dNm\text{-}rN_1\text{-}rN_2 \ldots rNn\text{-}3'$$

wherein dN represents a deoxyribonucleotide selected from among dAMP, dCMP, dGMP and dTMP; m represents an integer equal to or greater than zero, preferably from 10 to 50; rN represents a ribonucleotide selected from among AMP, CMP, GMP and UMP, preferably GMP; and n represents an integer of at least one or greater, preferably from 3 to 7. Some obvious and well known in the art modifications in the structure of the CAP switch oligonucleotide, such as replacement of 1–10 nucleotides with random nucleotides, nucleotide analogs, or nucleotides labeled with different hapten groups (such as, for example, biotin, digoxigenin, and fluorescein), incorporation of a terminator nucleotide (such as, for example, 3'-amino NMP, 3'-phosphate NMP, and 3'-fluoro NMP), using partially double-stranded DNA containing extension of a single-stranded CAPswitch oligonucleotide sequence $5'\text{-}dN_1\text{-}dN_2\text{-} \ldots dNm\text{-}rN_1\text{-}rN_2 \ldots rNn\text{-}3'$, incorporation of restriction sites, and incorporation of promoter sequences for bacteriophage RNA polymerase, which simplify subsequent purification and cloning of the cDNA but which still retain subtantially the same functional activity as an unmodified CAPswitch oligonucleotide, i.e., mRNA 5'-end extension of full-length cDNA by reverse transcriptase using CAPswitch oligonucleotide as a template are within the scope of present invention.

Also included within the subject invention are cDNA library construction kits, for example, library construction kits which include the novel oligonucleotides according to the subject invention for use with PCR procedures.

The subject invention also concerns novel template switching oligonucleotides that can be used according to the subject method.

Also included within the scope of the present invention are kits that include in one or more containers template switching oligonucleotides of the invention.

CAPswitch technology. The methods and materials of the present invention is primarily based on the use of unique CAPswitch oligonucleotides in cDNA synthesis. The subject cDNA synthesis can include a step of first-strand cDNA from polyA+RNA using reverse transcriptase coupled with either second-strand cDNA synthesis or PCR amplification in a second step to generate a high yield of full-length ds cDNA. When included in the first-strand cDNA synthesis reaction mixture, the CAPswitch oligonucleotides create a short extended template. In the course of first strand cDNA synthesis, the reverse transcriptase enzyme stops at the 5' end of the mRNA template. The 5'-end typically includes a 7-methylguanosine CAP structure present on the 5' ends of all eukaryotic mRNAs. The enzyme terminal transferase activity then adds a few additional nucleotides, primarily deoxycytidine, to the 3'-end of the of the newly synthsized cDNA strand. The CAPswitch oligonucleotide, which has an oligo (rG) sequence at its 3' end, base pairs with the deoxycytidine-rich stretch of nucleotides present on the cDNA strand, creating an extended template. Reverse transcriptase then switches templates and continues synthesis of cDNA that is complementary to the CAPswitch oligonucleotide. The resulting full-length ss cDNA incorporates at its 3' end a sequence which is complementary to both the complete 5' end of the mRNA and the CAPswitch oligonucleotide sequence.

Identified herein is an oligonucleotide structure (CAPswitch oligonucleotide) which can provide for an efficient template switching reaction in the course of first-strand cDNA synthesis from poly(A)+RNA using, as a donor, 5'-capped full-length mRNA and, as the acceptor, a chemically synthesized oligonucleotide. Chimeric cDNA products having an oligonucleotide sequence at the 3'-end of full-length cDNA were revealed by subsequent amplification (e.g., 5'-RACE) using a combination of a gene-specific primer and a primer complementary to a portion of the template switching oligonucleotide. One set of oligonucleotides according to the present invention, having an arbitrary sequence at the 5' end and random sequence at the 3' end, are represented by the following polynucleotide sequences:

CzR1 5'-d(TGTAGCGTGAAGACGACAGAA)r(N)$_{12}$-3' (SEQ ID NO. 1)
CzR2 5'-d(TGTAGCGTGAAGACGACAGAA(N)$_{11}$)r(N)$_1$-3' (SEQ ID NO. 2)
CzR3 5'-d(TGTAGCGTGAAGACGACAGAA(N)$_{11}$)-3' (SEQ ID NO. 3)
CzR4 5'-d(TGTAGCGTGAAGACGACAGAAGGATG(N)$_9$)r(N)$_1$-3' (SEQ ID NO. 4)
Na21-N4 5'-d(TGTAGCGTGAAGACGACAGAA)r(N)$_4$-3' (SEQ ID NO. 5)
Na21-N8 5'-d(TGTAGCGTGAAGACGACAGAA)r(N)$_8$-3' (SEQ ID NO. 6)
NA21-N12 5'-d(TGTAGCGTGAAGACGACAGAA)r(N)$_6$-3' (SEQ ID NO. 7)

wherein d( ) represents a deoxyribonucleotide sequence; $(N)_{11\ and\ (N)9}$ represent, respectively, a random deoxyribonucleotide sequence 11 or 9 bases long of dAMP, dGMP, dCMP and dTTP in each base position; r(N)$_{1-16}$ represents a random sequence 1 to 16 bases long of AMP, GMP, CMP and UMP in each base position.

Based on the efficiency of amplification of 5'-ends (5'-RACE) of four human cDNAs (smooth muscle α-actin, smooth muscle γ-actin, cytoskeletal γ-actin and transferrin receptor and model RNAs with and without cap structure at the 5' end), and subsequent sequence analysis of amplified product, conservative structures have been identified at the 3' end of an oligonucleotide which can be used to generate a highly efficient CAP-dependent template switching reaction. Mutational analysis of conservative and non-conservative regions of the oligonucleotide sequence (see the sequences of additional analyzed CAPswitch oligonucleotides, SEQ ID NOS. 19–66) revealed that the highest efficiency of CAP-dependent template switching was achieved using a basic DNA-RNA chimeric CAPswitch oligonucleotide having an arbitrary sequence at its 5' end and a conservative oligo ribo(G) sequence at the 3' end. This oligonucleotide is represented by the general formula:

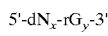

5'-dN$_x$-rG$_y$-3' long; and rG$_y$ represents an oligo rG sequence 3–5 bases long. The oligo rG sequence is responsible for the main template switching function associated with the CAPswitch oligonucleotide. The arbitrary deoxyribooligonucleotide sequence can be selected so as to be useful for subsequent cDNA synthesis and cloning steps.

In addition, the template switching reaction is most efficient for cDNAs that have sequence complementary to the 5' end of the mRNA, in comparison to cDNAs that were prematurely terminated during reverse transcription of the first strand and, therefore, do not have sequences complementary to the 5' end of the mRNA molecule. The presence of the CAP structure at the 5' end of mRNA is not a necessary requirement for template switching reaction, but the template switching reaction is most effective for full-length DNA products synthesized on mRNA which has the CAP structure present at the 5'-end.

Modifications in the structure of template switching oligonucleotides are contemplated within the scope of the present invention. Specifically, those modification which may affect the template switching efficiency but in which the template switching oligonucleotide retains the substantially the same functional activity as unmodifed template switching oligonucleotides, i.e., CAP-dependent extension of full-length cDNA by reverse transcriptase using the oligonucleotide as a template, is contemplated by the subject invention. The modified oligonucleotides can be used as alternatives to unmodified CAPswitch oligonucleotides. The following rules summarize these modifications that are useful according to the subject invention:

1a. The use of shorter (1–2 bases) oligo rG 3'-end sequences, replacement of one or several rG residue(s) for rA, rC or rU, or replacement of oligo rG for oligo dG reduces efficiency of the basic structure; longer oligo rG sequences (7–9 bases) do not significantly influence template switching efficiency.

1b. Modification of the 3' terminal G at the 3'-OH group of ribose residue by an amino, biotin, phosphate, fluoro or glycerol group can significantly reduce background in subsequent PCR amplification steps (step 3A).

1c. Changes in the sequence of the arbitrary portion of a template switching oligonucleotide, replacement partially or completely deoxyribonucleotides for ribonucleotides, including restriction site(s), does not significantly influence template switching efficiency. Using a longer arbitrary sequence (about 22 to 42 bases) at the 3'-end of the template switching oligonucleotide reduces the efficiency of template switching, whereas shorter sequences (about 15 to 17 bases) slightly increase the efficiency of template switching but make subsequent PCR amplification steps (step 3A, 3C) less efficient.

1d. A person skilled in this art having the benefit of the current disclosure would recognize that other modifications in the structure of template switching oligonucleotides of the present invention can be readily prepared. These modifications can increase the efficiency and specificity of the CAP-dependent template switching reaction. For example, using aptamer (random oligonucleotide) selection technology (Kenan et al., 1994) it is possible to find ribonucleotide or deoxyribonucleotide sequences of the arbitrary portion of the template switching oligonucleotide which efficiently bind to the CAP structure of an mRNA molecule and, therefore, increase efficiency of the template switching reaction. The same result can be achieved by replacement of natural nucleotide(s) with modified nucleotides in order to increase the affinity of the template switching oligonucleotides binding to the CAP structure.

Chimeric protein-template switching oligonucleotides can also be constructed so that the protein portion recognizes and binds the CAP structure, which can increase efficiency of the template switching reaction. These cap binding proteins or protein portions are well known in the art and preferably include antibodies against the CAP structure and eukaryotic initiation factor 4E (eIF-4E).

Another advantage of using the methods and compositions of the present invention is the high flexibility of this procedure which makes it possible to use this new technology with conventional cDNA cloning procedures well known in art. Advantageously, the subject invention can eliminate the need for multiple enzymatic or purification procedures used in conventional procedures. The subject method can provide CAP-dependent automatic and direct addition of a template switching oligonucleotide sequence to the 5' end of mRNA:cDNA hybrid in the course of first-strand cDNA synthesis. Moreover, the methods and compositions of the subject invention can be combined with procedures well known in the art for cDNA synthesis and cloning. It will be apparent to those skilled in the art that the order of some of the individual steps, the exact structure of CDS primers, and the vectors used for cDNA library construction can be varied. Thus, modifications, substitutions, and optimization of the methods and materials disclosed herein which provide for the cloning of full-length cDNA or cDNA fragment(s) containing complete complementary nucleotide sequence of the 5'-end of mRNA molecules are within the scope of the present invention. The description below details only preferred steps which result in the efficient generation of full-length cDNA from RNA.

First-strand cDNA synthesis. Using the subject method with conventional procedures, first-strand cDNA synthesis can be carried out using an annealed complex comprising a cDNA synthsis primer:mRNA as a template for reverse transcription. Primer extension can be catalyzed by reverse transcriptase, or by a DNA polymerase possessing reverse transcriptase activity, in the presence of adequate amounts of other components necessary to perform the reaction, for example, deoxyribonucleoside triphosphates ATP, CTP, GTP and TTP, $Mg^{2+}$, optimal buffer. A variety of DNA polymerases possessing reverse transcriptase activity can be used for the first-strand cDNA synthesis. Examples of DNA polymerases that can be used in the methods of the present invention include the DNA polymerases derived from organisms such as thermophilic bacteria and archaebacteria, retroviruses, yeast, Neurospora, Drosophila, primates and rodents. Preferably, the DNA polymerase is isolated from Moloney murine leukemia virus (M-MLV) (U.S. Pat. No. 4,943,531) or M-MLV reverse transcriptase lacking RNaseH activity (U.S. Pat. No. 5,405,776), human T-cell leukemia virus type I (HTLV-I), bovine leukemia virus (BLV), Rous sarcoma virus (RSV), human immunodeficiency virus (HIV) or *Thermus aquaticus* (Taq) or *Thermus thermophilus* (Tth) (U.S. Pat. No. 5,322,770). These DNA polymerases may be isolated from an organism itself or, in some cases, obtained commercially. DNA polymerases useful with the subject invention can also be obtained from cells expressing cloned genes encoding the polymerase. As a starting material for cDNA synthesis, poly(A)+RNA or total RNA from yeast and higher organisms such as plants or animals can be used.

The first-strand cDNA synthesis step of the subject method can include template switching oligonucleotides of the present invention in the reaction mixture, but are not a necessary component for carrying out first-strand cDNA synthesis. The template switching oligonucleotides can be added at the time of the template switching step which follows the first-strand synthesis step. Thus, it is understood that template switching oligonucleotide molecules can be included in the first-strand reaction composition (for example, during cDNA synthesis primer annealing to RNA or when contacting the RNA with an enzyme possessing reverse transcriptase activity) or the oligonucleotides can be added in the course of, or after completion of, the first-strand cDNA synthesis reaction.

Depending on the strategy to be employed for cDNA cloning, numerous cDNA synthesis primers structures can be used for the first-strand cDNA synthesis using poly(A)+RNA as a template and catalyzed by the reverse transcriptase activity. The cDNA synthesis primer can be a single-stranded oligonucleotide, a double-stranded oligonucleotide having a single-stranded portion (primer-restriction-end or PRE, adapter, as described by Coleclough et al., 1985), or a vector primer, representing ds vector with a single-stranded portion (Okayama et al., 1982). In all three cases, a single-stranded portion of the cDNA synthesis primer is responsible for binding with poly(A)+RNA and initiating the first-strand cDNA synthesis. In a preferred embodiment of the subject method, for full-length cDNA library construction, a CDS primer containing an oligo dT tail at the 3'-end of the primer is annealed to the poly(A) portion of mRNA. For rapid amplification or cloning of 5' cDNA ends and for selective cloning of particular genes, the CDS primer can possess a random sequence or arbitrary sequence which may correspond to a particular sequence of a target gene which is to be cloned.

The subject invention particularly concerns the embodiments of the above methods wherein the CDS primer can be annealed to:

1a. The poly(A) tail of poly(A)+RNA. The cDNA synthesis primer can be selected from a single-stranded oligonucleotide, any partially double-stranded DNA fragment, or any linear vector primer. In a preferred embodiment, the oligonucleotide primer has the sequence: 5'-$dN_1$-$dN_2$- . . . $dNm$-$dTn$-$dN_1$-$dN_2$- . . . $dNp$-3' wherein m represents an integer 0 and above, preferably from 0 to 20; n represents an integer 8 and above, preferably from 8 to 30; p is preferably from 0 to 3; dN represents a deoxyribonucleotide selected from or represent mixture of dAMP, dCMP, dGMP, and dTMP; dT represents dTMP. Some modifications in the structure of the primer such as replacement of 1–10 nucleotides for nucleotides containing different hapten groups (biotin, digoxigenin, fluorescein, etc.), nucleotide analogs, ribonucleotides, non-natural nucleotides, incorporation of restriction sites, bacteriophage RNA polymerase promoter region which simplify subsequent purification, using and cloning cDNA but still retain the main function of the primer, i.e., priming activity from poly(A) portion of poly(A)+RNA, are within the scope of present invention. Using a partially double-stranded DNA primer or linear plasmid vectors having a single-stranded tail sequence 5'-$dN_1$-$dN_2$- . . . $dNm$-$dTn$-$dN_1$-$dN_2$- . . . $dNp$-3', described above, and possessing priming activity for first-strand cDNA synthesis from poly(A) portion of poly(A)+RNA, are also considered as part of the subject invention. In order to simplify the cloning procedure, the CAPswitch oligonucleotide can be attached to the other end of vector primer. In this case, the vector primer will possess at one end a sequence corresponding to the CDS primer and, at the other end, the CAPswitch oligonucleotide (CAPswitch-vector primer technology). Subsequent cDNA synthesis and automatic template switching will generate cDNA:vector chimeric product, which can be easily cloned as described Okayma et al., 1982.

1b. Inner, non-poly(A) portion of the mRNA. These oligonucleotide primer(s) have the general formula $dN_1$-$dN_2$- . . . $dNq$, where dN represents a deoxyribonucleotide selected from among dAMP, dCMP, dGMP, and dTMP or represent a mixture of 2–4 of these bases; and q represents integer 6 and above, preferably from 6 to 50. These primers can have a random sequence, i.e., annealed to all mRNAs, an arbitrary sequence, Le., annealed to at least one arbitrary mRNA, or a sequence complementary to at least one mRNA. Also, the sequence of these primer(s) can include a restriction site(s) or modified bases (for example, biotinylated) to facilitate subsequent purification or cloning procedure.

Second-strand cDNA synthesis and/or PCR amplification. First-strand cDNA synthesis based on CAPswitch technology generates a full-length (or the corresponding 5' end of a full-length fragment) mRNA:cDNA hybrid molecule intermediates flanked by a CDS primer at its 3' end, and a CAPswitch oligonucleotide at its 5' end. Such intermediates can be easily converted to a ds cDNA form suitable for subsequent cloning using conventional procedures. These procedures are well known and include:

1. Direct amplification of full-length cDNA by combination of PCR primer corresponding CDS and CAPswitch flanking portions of mRNA:cDNA hybrid and effective amount of other reagents under conditions necessary to perform PCR. Preferably, the conditions are those developed for amplification of long nucleic acid sequences and described by Cheng (International Patent (1995)) and Barnes (U.S. Pat. No. 5,436,149 of Jul. 25, 1995).

2. Replacement of the mRNA portion of the mRNA:cDNA hybrid with a second-strand cDNA essentially as described by Okayama et al. (1982) and Gubler et al. (1983). This process entails digestion of the RNA with a ribonuclease such as E. coli RNase H repair synthesis using a DNA polymerase having the activities of DNA polymerase I, and ligation. The procedure depends on the structure of the CDS primer used for the first-strand cDNA synthesis. Second-strand cDNA synthesis can be carried out using as a template mRNA:cDNA hybrid or mRNA:cDNA:vector chimeric product using vector primer for first-strand synthesis (CAPswitch-vector primer technology, see above). Alternatively, mRNA:cDNA hybrid generated by PRE adaptor strategy, described above, can be digested at the 5' and 3' flanking sequences, which correspond to PRE adaptor and CAPswitch oligonucleotide by at least one restriction enzyme, and then ligated into a conventional vector digested by the same restriction enzyme(s). Any restriction enzyme(s) can be used as long as it does not cut within mRNA:cDNA hybrid.

Cloning into vector. In the case of using a vector primer (CAPswitch-vector primer) or PRE adaptor strategy, the ds cDNA generated after second-strand cDNA synthesis is already inserted into the vector and does not require this step. When an oligonucleotide CDS primer is used, the ds cDNA prepared in the second step by PCR or by mRNA replacement technology can be ligated with adaptors or digested with restriction enzyme(s) in sequences corresponding to CDS and CAPswitch oligonucleotide flanking portions, thus generating ds cDNA molecules which will be ligated to any conventional cloning vector (including plasmid, cosmid, phage, retroviral vector and so on) after digesting it with the same restriction enzyme(s).

Then, recombinant DNA molecules comprising a full-length cDNA library can be introduced into prokaryotic hosts and, optionally, eukaryotic hosts, useful in the high frequency cloning of full-length ds cDNA and in the expression of recombinant proteins therefrom.

Once cloning is completed according to the invention, the desired clone(s) can be detected by labeled probe, monoclonal or polyclonal antibodies prepared against the product in a conventional immunoassay or enriched for desired target by hybridization selection approach, described for example by Li et al. in International Patent WO 95/04745 of 9 Aug. 1994.

Summary. Use of CAPswitch oligonucleotide in cDNA synthesis and cloning significantly simplify and improve technology of full-length cDNA library construction. The main benefits are as follows:

1. The one-stage procedure which includes first-strand cDNA synthesis and addition of a defined sequence to the 3' end of cDNA which significantly reduces the number of steps (from 5–7 to 2–3 steps) necessary for conventional PCR-based standard cDNA library construction technology. A lower number of steps means that the novel methods and materials of the present invention is more efficient, easier, less labor-intensive, and more reproducible than conventional cDNA library construction methods.

2. In accordance with the present invention, the CAP-dependent template switching mechanism provides significantly more efficient technology for synthesizing full-length cDNA and generating cDNA libraries mostly containing full-length cDNAs. The methods and materials of the present invention can provide a novel method for readily selecting the full-length cDNAs to be cloned in the cDNA library.

As used herein, the term "full-length complementary DNA or cDNA" is defined as a full-length single-stranded (ss) or double-stranded (ds) cDNA(s) or cDNA fragment(s) which contain the complete sequence information of the 5'-end(s) of mRNA(s). Full-length cDNA can contain the complete sequence information of the 5'-end of a particular (target) mRNA or of the whole population of polyA+RNA used as a template for the first-strand cDNA synthesis.

As used herein, the term "full-length cDNA library" refers to the whole population of ss or ds cDNAs synthesized from polyA+RNA as a template. The full-length cDNA library can be used directly for different applications known in the art or it can be cloned into any suitable recombinant cloning vehicle, and host can be transformed with the cloning vehicle.

The term "template switching" reaction refers to a process of template-dependent synthesis of the complementary strand by a DNA polymerase using two templates in consecutive order and which are not covalently linked to each other by phosphodiester bonds. The synthesized complementary strand will be a single continuous strand complementary to both templates. Typically, the first template is polyA+RNA and the second template is a template switching or "CAP switch" oligonucleotide.

As used herein, the term "arbitrary sequence" or "anchor sequence" refers as any defined or pre-selected deoxyribonucleotide, ribonucleotide or mixed deoxyribo/ribonucleotide sequence which contains a particular sequence of natural or modified nucleotides.

As used herein, the term "random sequence" is defined as deoxyribonucleotide, ribonucleotide or mixed deoxyribo/ribonucleotide sequence which contains in each nucleotide position any natural or modified nucleotide.

As used herein, the term "full-length anchored cDNA" is defined as a full-length ss cDNA which has a defined arbitrary sequence at the 3'-end.

As used herein, the term "mRNA:cDNA hybrid" refers to a product after first-strand cDNA synthesis catalyzed by reverse transcriptase using polyA+RNA as a template. "mRNA-cDNA hybrid" can be full-length if the cDNA portion includes the complete sequence of the 5'-ends of the template mRNA.

As used herein, the term "reverse transcriptase" is defined as any DNA polymerase possessing reverse transcriptase activity which can be used for first-strand cDNA synthesis using polyA+RNA or total RNA as a template.

As used herein, two sequences are said to be "complementary" to one another if they are capable of hybridizing to one another to form antiparallel, double-stranded nucleic acid structure.

As used herein, the term "hapten" refers to a molecule that is bound to a nucleic acid molecule and can be recognized and bound by another molecule, or "binding ligand," e.g., an antibody, streptavidin and biotin, transient metal, and others known in the art. Examples of haptens include chelating group, biotin, fluorescein, digoxigenin, antigen, and others known in the art.

As used herein, the term "solid support" refers to any known substrate which can be used for the immobilization of a binding ligand or oligonucleotide/polynucleotide sequences used by any known method.

As used herein, the term "reporter group" refers to any group incorporated into full-length cDNA by conventional chemical or enzymatic labeling procedures and which can be detected by use of conventional techniques, such as scintillation counting, autoradiography, fluorescence measurement, calorimetric measurement, light emission measurement, and other means known in the art. Examples of reporter groups include radioisotopes, fluorescent, chemifluorescent, chemiluminescent, hapten groups, and others known in the art.

As used herein, the term "subtractive hybridization" refers to technology which allows for the recovery of a cDNA population containing a highly enriched representation of the cDNA species that are present in one cDNA population (tester), but that are less abundant or not found in another cDNA population (driver). Examples of subtractive hybridization technologies include Suppression Subtractive Hybridization technology (Chenchik et al. U.S. Pat. No. 5,565,340), representation difference analysis (Wigler et al., U.S. Pat. No. 5,436,142); and linker capture subtraction (Yang et al., Anal. Biochem. 237:109–114(1996).

As used herein, the term "nucleotide analog" refers to a nucleotide which is not typically found in the in DNA or RNA and possesses some additional features which can improve efficiency of the template switching reaction or improve the usage of anchored cDNA generated. For example, suitable nucleotide analogs include modification in the base or sugar-phosphate backbone, like peptide nucleic acid, inosin, 5-nitroindole deoxyribofuranosyl, 5-methyldeoxycytosine, and 5,6-dihydro-5,6-dihydroxydeoxythymidine. Other nucleotide analogs will be evident to those skilled in the art.

Following are examples which illustrate procedures for practicing the invention. These examples should not be construed as limiting. All percentages are by weight and all solvent mixture proportions are by volume unless otherwise noted.

EXAMPLE 1

Figure 2:
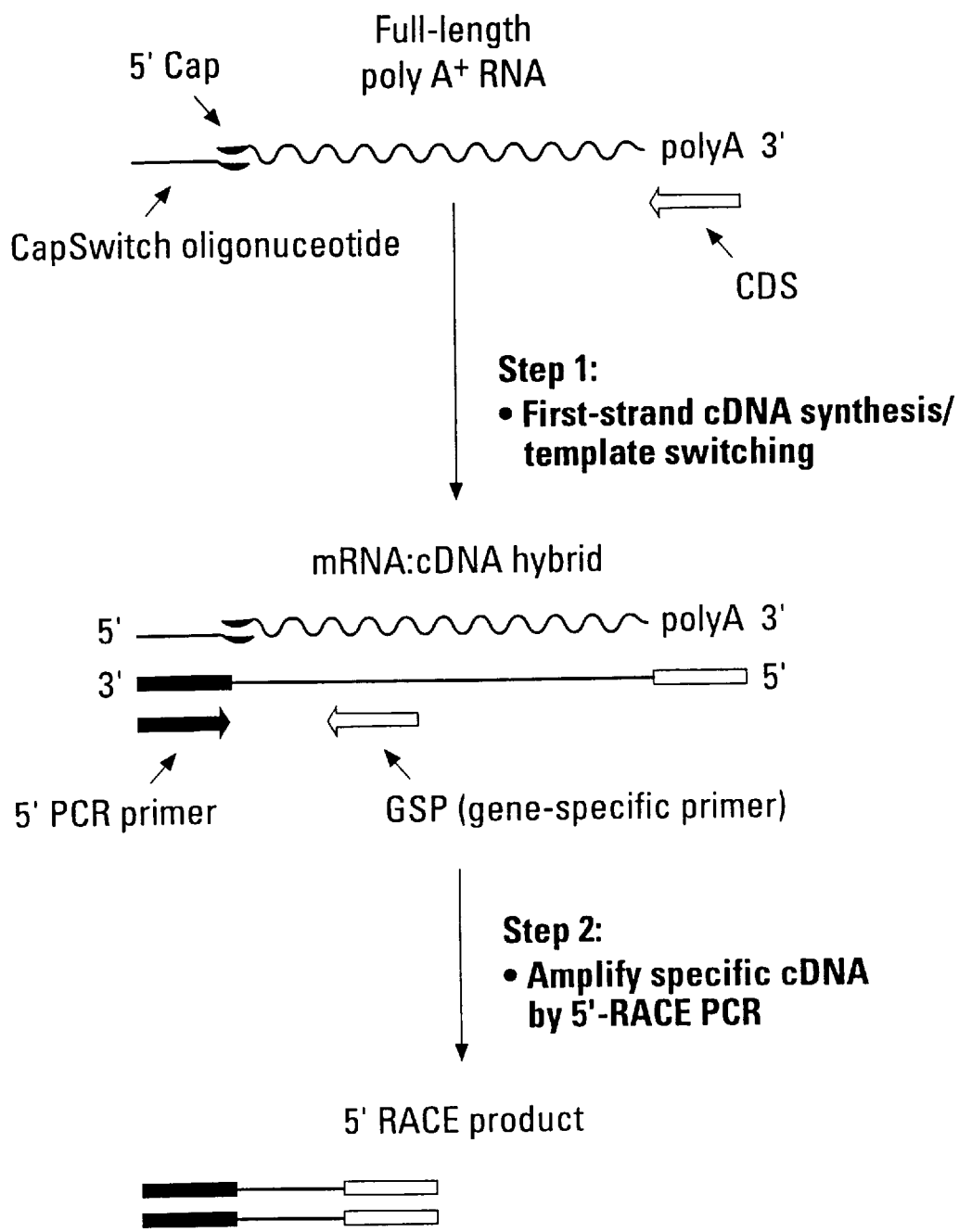
FIG. 2 shows a representation of a procedure using the methods and materials of the present invention for cloning 5'-end sequence of full-length DNA.

Preferred Method for Cloning 5'-end Sequences of Full-Length cDNA Based on CAPswitch Technology Obtaining a full-length cDNA is one of the most important, and often one of the most difficult, tasks in characterizing genes. Traditional methods for cDNA library construction usually produce only partial cDNA fragments. To facilitate recovery of the rest of the coding sequence, an in vitro method for the rapid amplification of cDNA ends (RACE) was proposed in 1988 (Frohman et al., 1988). In spite of various modifications which have been developed, the current RACE technologies are complicated and inefficient. The methods and materials of the present invention provides a method which significantly simplifies and makes more efficient the 5'-RACE procedure. The flow chart which describes CAPswitch-based 5'-RACE procedure is shown in FIG. 2, and the preferred protocol is described below. Some obvious modifications in protocol, e.g., using other enzymes possessing similar enzymatic activities for first-strand synthesis step and PCR, using other sequences of oligo(dT) primer and CAPswitch oligonucleotide, using for first-strand synthesis a gene-specific primer, instead of a oligo (dT) primer, all fall within the scope of the present invention.

Step. 1 First-strand cDNA synthesis-template switching procedure.

10 pmol of cDNA synthesis primer (oligo d(T) primer) CDS1: 5'-d(TCTAGAATTCAGCGGCCGC(T)$_{30}$VN) -3' (SEQ ID NO. 8)

(where V=G or A or C; N=G or A or T or C) and 50 pmol of CAPswitch oligonucleotide (CSO1):

CSO1: 5'-d(CTAATACGACTCACTATAGGGC)r(GGGp)-3' (SEQ ID NO. 9)

(where p is 3'-phosphate group) were annealed to 1 μg of human placenta poly(A)$^+$RNA (CLONTECH Laboratories, Inc., Palo Alto, Calif.), in a volume of 5 μl of deionized water, by heating the mixture for 2 minutes at 70° C., followed by cooling on ice for 2 minutes. First-strand cDNA synthesis was then initiated by mixing the annealed primer-RNA with 200 units of M-MLV RNase H- reverse transcriptase (SuperScript II reverse transcriptase, Life Technologies) in a final volume of 10 μl, containing 50 mM Tris-HCl (pH 8.3 at 22° C.); 75 mM KCl; 6 mM MgCl$_2$; 1 mM DTT; and 1 mM each of dATP, dGTP, dCTP, and dTTP. The first-strand cDNA synthesis-template switching reaction was incubated at 42° C. for 1.5 hours in an air incubator and then cooled on ice. We also synthesized first-strand cDNA using random d(N)$_6$ primers (500 ng) or human beta-actin antisense gene-specific primer:

ACT1: 5'-d(ACTCGTCATACTCCTGCTTGCTGATCC ACATCTGC)-3' (SEQ ID NO. 10)

or human transferrin receptor antisense gene-specific primer:

TFR1: 5'-d(GTCAATGTCCCAAACGTCACCAGAGA)-3' (SEQ ID NO. 11)

instead of the oligo d(T) primer.

The reaction mixture was then diluted 500-fold by addition of 5 ml of 10 mM Tricine-KOH (pH 8.5 at 22° C.) and 0.1 mM EDTA, incubated at 94° C. for 1.5 min, cooled on ice, and stored at −20° C.

Step 2. 5'-RACE.

PCR amplification was performed using the Advantage KlenTaq Polymerase Mi (CLONTECH Laboratories, Inc.). This kit contains a mixture of KlenTaq-1 and Deep Vent DNA polymerases (New England Bio Labs) and TaqStart antibody (CLONTECH Laboratories, Inc.). The TaqStart antibody provides automatic hot-start PCR. Amplification was conducted in a 50-μl volume containing 5 μl of diluted first-strand cDNA; 40 mM Tricine-KOH (pH 9.2 at 22° C.); 3.5 mM Mg(OAc)$_2$; 10 mM KOAc; 75 μg/ml BSA; 200 μM each of dATP, dGTP, dCTA, and dTTP; 0.2 μM each of CAPswitch primer (CSP1): 5'-d (CTAATACGACTCACTATAGGGC)-3' (SEQ ID NO. 12) and gene-specific primer (GSP 1 for beta-actin or transferrin receptor); and 1 μl of 50× KlenTaq Polymerase Mix. Temperature parameters of the PCR reactions were as follows: 1 minute at 94° C. followed by 5 cycles of 94° C. for 30 seconds and 72° C. for 5 minutes; then 5 cycles of 94° C. for 30 seconds and 70° C. for 5 minutes; then 25 cycles of 94° C. for 30 seconds and 68° C. for 5 minutes; followed by a 10-minute final extension at 68° C. PCR products were examined on 1.2% agarose/EtBr gels in 1× TBE buffer. As a DNA size marker we used a 1 kb DNA Ladder (Life Technologies).

Both human beta-actin and transferrin receptor cDNA 5'-RACE reaction generate a single band which correspond to the expected size of full-length amplified 5'-RACE product. Subsequent cloning and sequence analysis of 18 randomly picked 5'-RACE clones confirm their identity to beta-actin and transferrin receptor 5'-end fragments. Moreover, 5'-end sequences of amplified 5'-RACE product exactly correspond to sequences of full-length beta-actin and transferrin receptor mRNAs followed by sequences corresponding to CAPswitch oligonucleotide. This example illustrates that CAPswitch 5'-RACE can be efficiently used not only for amplification of full-length 5'-end sequences of cDNAs but also for exact mapping of transcriptional start sites.

EXAMPLE 2

CAPswitch PCR-Based Technology for Full-Length cDNA Library Construction

Figures 1, 3:
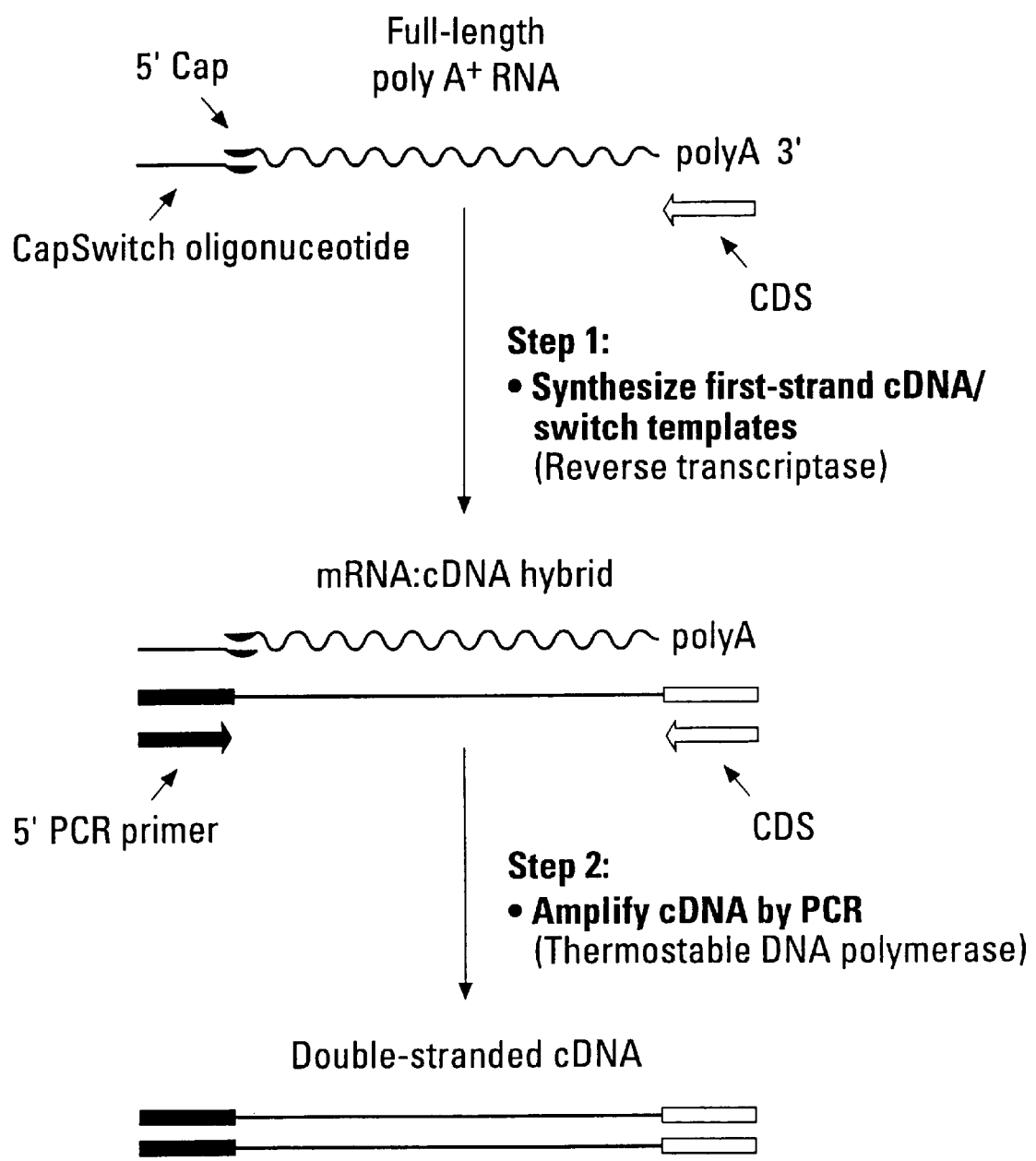
FIG. 3 shows a representation of PCR-based methods and materials of the present invention for full-length cDNA library construction according to the subject invention.
Figures 2, 3:
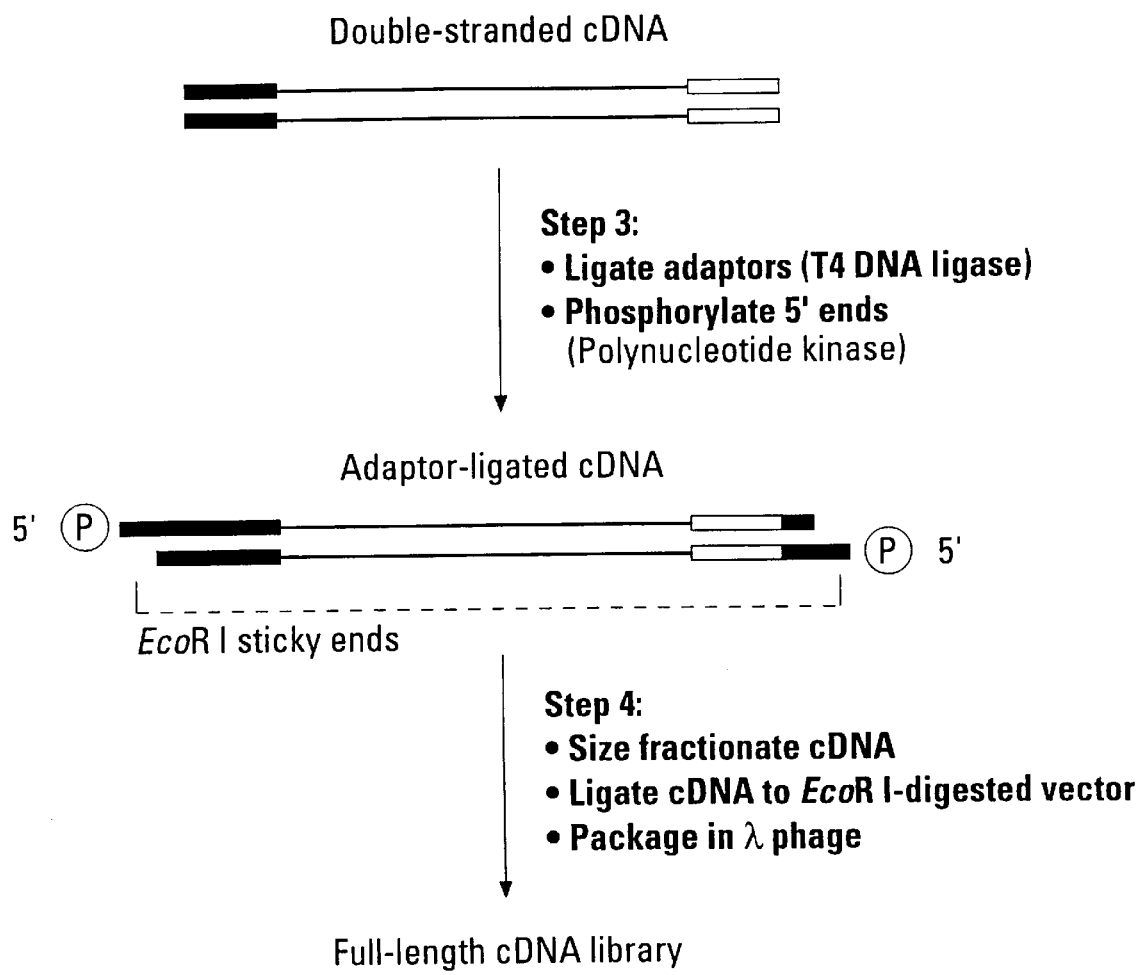

Methods and materials of the present invention can be effectively used for construction of cDNA libraries using as a template 10–100 ng of total RNA. Any conventional procedure well known in art can be used to purify this small amount of total RNA from 10–50 mg of "difficult" cells or tissues, like human biopsy tissues, pathogenic microorganisms, tissues at different developmental stages and so on. The flow chart in FIG. 3 shows the main step of this procedure. It will be apparent to those skilled in the art that some individual non-essential steps, structure of CDS primer, CAPswitch oligonucleotide and adaptors shown in FIG. 3 can be varied without changing the efficiency of the whole procedure. For example, instead of the adaptor ligation step (step 3), ds cDNA generated by PCR can be digested by rare cutting restriction endonuclease(s) in sequences corresponding CDS and CAPswitch oligonucleotide flanking portions and cloned directly into vector. Also, other conventional procedures well known in the art for direct cloning of PCR product, such as TA-cloning vector, blunt end ligation, and the like, can be used for cloning and generation of CAPswitch full-length cDNA libraries. Any such variations in the preferred protocol which are based on using methods and materials of the subject invention are within the scope of the invention.

Step 1. First-strand synthesis—template switching.

10 pmol of cDNA synthesis primer (oligo d(T) primer) CDS1:

5'-d(TCTAGAATTCAGCGGCCGC(T)$_{30}$VN)-3' (SEQ ID NO. 8)

(where V=G or A or C; N=G or A or T or C) and 10 pmol of CAPswitch oligonucleotide (CSO2):

CSO2: 5'-d(CTAATACGACTCACTATAGGGC)r(GGG)-3' (SEQ ID NO. 13)

were annealed to 100 ng of human skeletal muscle Total RNA (CLONTECH Laboratories, Inc.) in a volume of 5 µl of deionized water by heating the mixture for 2 minutes at 70° C., followed by cooling on ice for 2 minutes. First-strand cDNA synthesis was then initiated by mixing the annealed primer-RNA with 200 units of M-MLV RNase H- reverse transcriptase (SuperScript II reverse transcriptase, Life Technologies) in a final volume of 10 µl, containing 50 mM Tris-HCl (pH 8.3 at 22° C.); 75 mM KCl; 6 mM MgCl$_2$; 1 mM DTT; and 1 mM each of dATP, dGTP, dCTP, and dTTP. The first-strand cDNA synthesis-template switching reaction was incubated at 42° C. for 1.5 hours in an air incubator and then cooled on ice.

Step 2. Generation of full-length cDNA by PCR.

PCR amplification of full-length cDNA was performed using the Advantage KlenTaq Polymerase Mix (CLONTECH Laboratories, Inc.). Amplification was conducted in a 100-µl volume containing 2 µl of first-strand cDNA; 40 mM Tricine-KOH (pH 9.2 at 22° C.); 3.5 mM Mg(OAc)$_2$, 10 mM KOAc; 75 µg/ml BSA; 200 µM each of dATP, dGTP, dCTP, and dTTP; 0.2 µM each of CAPswitch primer (CSP1) and CDS1 primer 1; and 1 ml of KlenTaq Polymerase mix. Temperature parameters of the PCR reactions were as follows: 1 minute at 95° C. followed by 20–22 cycles of 95° C. for 15 seconds and 68° C. for 5 minutes; followed by a 10-minute final extension at 68° C. PCR products were examined on 1.2% agarose/EtBr gels in 1× TBE buffer. As a DNA size marker we used a 1 kb DNA Ladder (Life Technologies).

Step 3. Adaptor ligation.

The 50 µl of ds cDNA generated at the PCR step were combined with 2 µl of Proteinase K (2 mg/ml) and incubated at 45° C. for 1 hour, followed by a denaturation step at 70° C. for 10 minutes. Then, 3 µl (15 units) of T4 DNA polymerase were added to the reaction mixture and additionally incubated at 16° C. for 30 minutes. ds cDNA was then precipitated by addition of a half volume of 4 M ammonium acetate (about 35 µl) and 3.7 volumes of 95% ethanol (about 260 µl). After vortexing, the tube was immediately centrifuged at 14,000 r.p.m. in a microcentrifuge for 20 minutes. The pellet was washed with 80% ethanol without vortexing, centrifuged as above for 10 minutes, air dried, and dissolved in 16 µl of deionized water. The ds cDNA was then ligated to an adaptor overnight at 16° C. under the following conditions: 16 µl of ds cDNA solution, 50 mM Tris-HCl (pH 7.8 at 22° C.), 10 mM MgCl$_2$, 1 mM DTT, 1 mM ATP, 5% polyethylene glycol (M.W. 8,000), 2 µM of adaptor (Ad1):

Ad1: 5'-d(AATTCGCGGCCGCGTCGAC)-3'     (SEQ ID NO. 14)

3'-d(GCGCCGGCGCAGCTGp)-5'     (SEQ ID NO. 15)

(where p=a 3'-phosphate group) and 1 unit of T4 DNA ligase (Life Technologies) in a total volume of 30 µl. The ligation mixture was then stopped by addition of 70 µl of 10 mM EDTA. The ds cDNA was extracted once with phenol/chloroform/isoamyl alcohol (25:24:1, vol/vol), once with chloroform/isoamyl alcohol (24:1, vol/vol), and then precipitated by addition of 10 µl of 3 M sodium acetate and 250 µl of 95% ethanol. After vortexing, the tube was immediately centrifuged at 14,000 r.p.m. in a microcentrifuge for 20 minutes. The pellet was washed with 80% ethanol without vortexing, centrifuged as above for 10 minutes, air dried, and dissolved in 20 µl of deionized water. The adaptor ligated ds cDNA was then phosphorylated at 37° C. for 30 minutes under the following conditions: 20 µl of adaptor-ligated ds cDNA solution, 50 mM Tris-HCl (pH 7.8 at 22° C.), 10 mM MgCl$_2$, 1 mM DTT, 1 mM ATP, 30 units of T4 polynucleotide kinase (Epicenter Technology) in a final volume 30 µl. Then phosphorylation reaction was terminated by adding 2 µl of 0.2 M EDTA and heat inactivated at 70° C. for 15 minutes.

Step 4. cDNA Size fractionation and cloning.

Phosphorylated adaptor-ligated ds cDNA generated at the previous step was fractionated on the 1.2 ml Sephacryl S500 0 (Phamacia) gel filtration column equilibrated by 10 mM Tris-HCl (pH 7.4), 30 mM NaCl, 0.5 mM EDTA Size distribution of cDNA in the fractions was analyzed by 1.1% agarose/EtBr gel alongside a 1 kb DNA size marker (Life Technologies). Fractions corresponding to cDNA sizes longer than 0.5 kb were pooled together (total volume 250 µl) and precipitated by adding 1/10 volume (25 µl) of 3 M sodium acetate, 1.5 µl of 20 mg/ml glycogen and 2.5 volume (400 µl) of 95% ethanol.

After vortexing, the tube was immediately centrifuged at 14,000 r.p.m. in a microcentrifuge for 20 minutes. The pellet was washed with 80% ethanol without vortexing, centrifuged as above for 10 minutes, air dried, and dissolved in 15 µl of deionized water. The ds cDNA was then ligated to the λgt11 EcoRI vector arm (CLONTECH Laboratories, Inc.) overnight at 16° C. under the following conditions: 5 µl of ds cDNA solution, 50 mM Tris-HCl (pH 7.8 at 22° C.), 10 mM MgCl$_2$, 1 mM DTT, 1 mM ATP, 5% polyethylene glycol (M.W. 8,000), 2.5 µg of λgt11 EcoRI arms, and 2.5 units of T4 DNA ligase (Life Technologies) in a total volume of 25 µl. The ligation mixture was then packaged using standard protocols as described in the laboratory manual by Sambrook et al. (1989).

In order to confirm the high quality of the library generated using the methods and compositions of the present invention, 50 recombinant phage clones were selected at random for the determination of insert size. The size distribution of the inserts was in the range of 0.5–4.5 kb with a maximum of 2.0–3.0 kb that correspond to the size distribution of skeletal muscle poly(A)+RNA in Total RNA used for cDNA library construction. The same 50 inserts were sequenced using Delta Tth DNA polymerase Sequencing kit (CLONTECH Laboratories, Inc.). Ten of the sequences were identified in a search of the GenBank database. They are transferrin receptor, ribosomal protein L7, myosin light chain 2, LIM domain protein, ATPase factor 6, cytochrome C oxidase, cytoskeletal γ-actin, smooth muscle α-actin, and smooth muscle γ-actin. For three cDNAs the sequences of the clones were longer than published in GenBank. For seven cDNAs, their sequences exactly corresponded to full-length mRNA sequences starting from the cap site.

These data show that methods and compositions of the present invention can be used for cDNA library construction to generate a high quality cDNA library with a very high level of full-length cDNA clones.

EXAMPLE 3

Figures 1, 4:
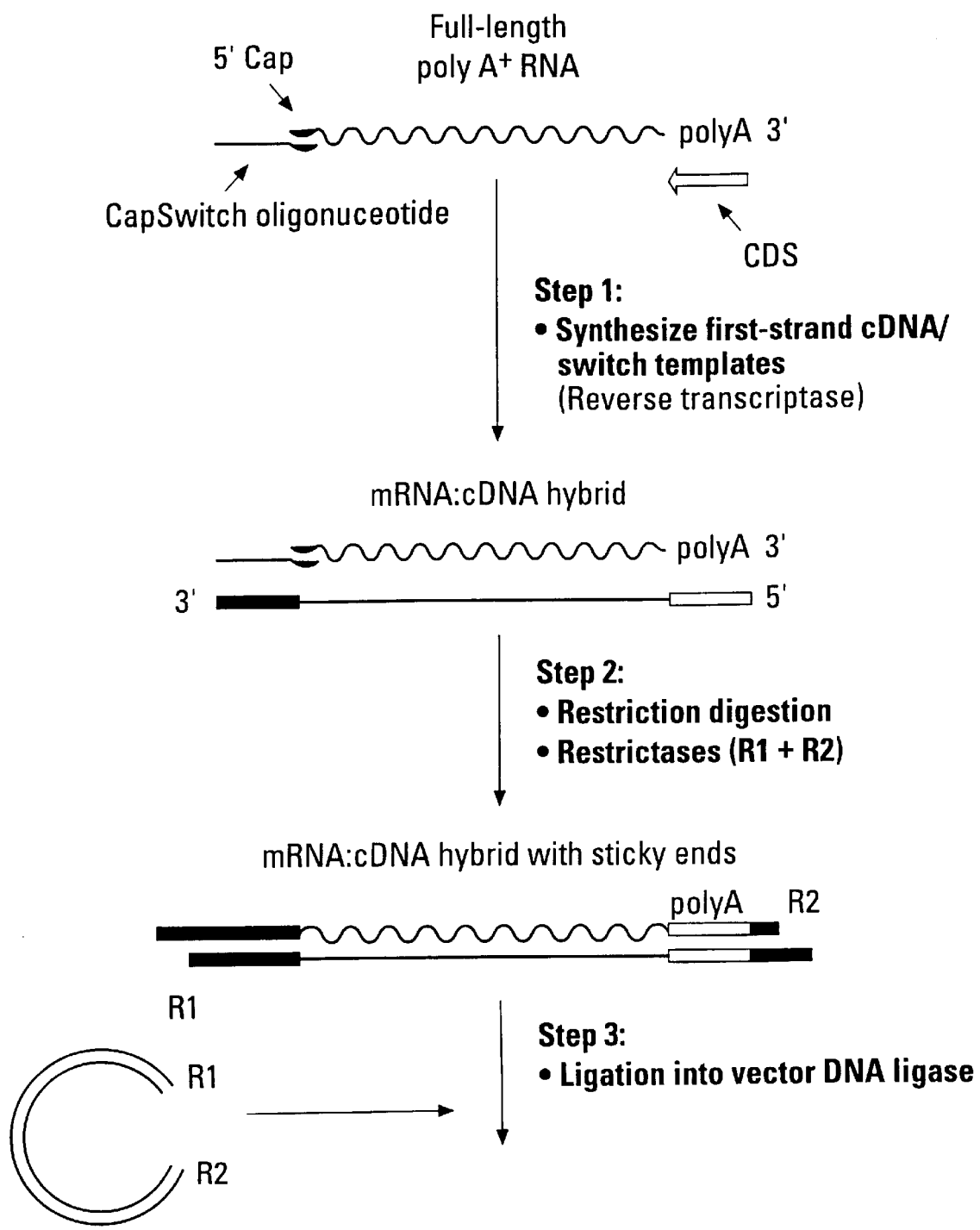
FIG. 4 shows a representation of CAPswitch full-length cDNA library construction technology based on PRE adaptor-primer strategy.
Figures 2, 4:
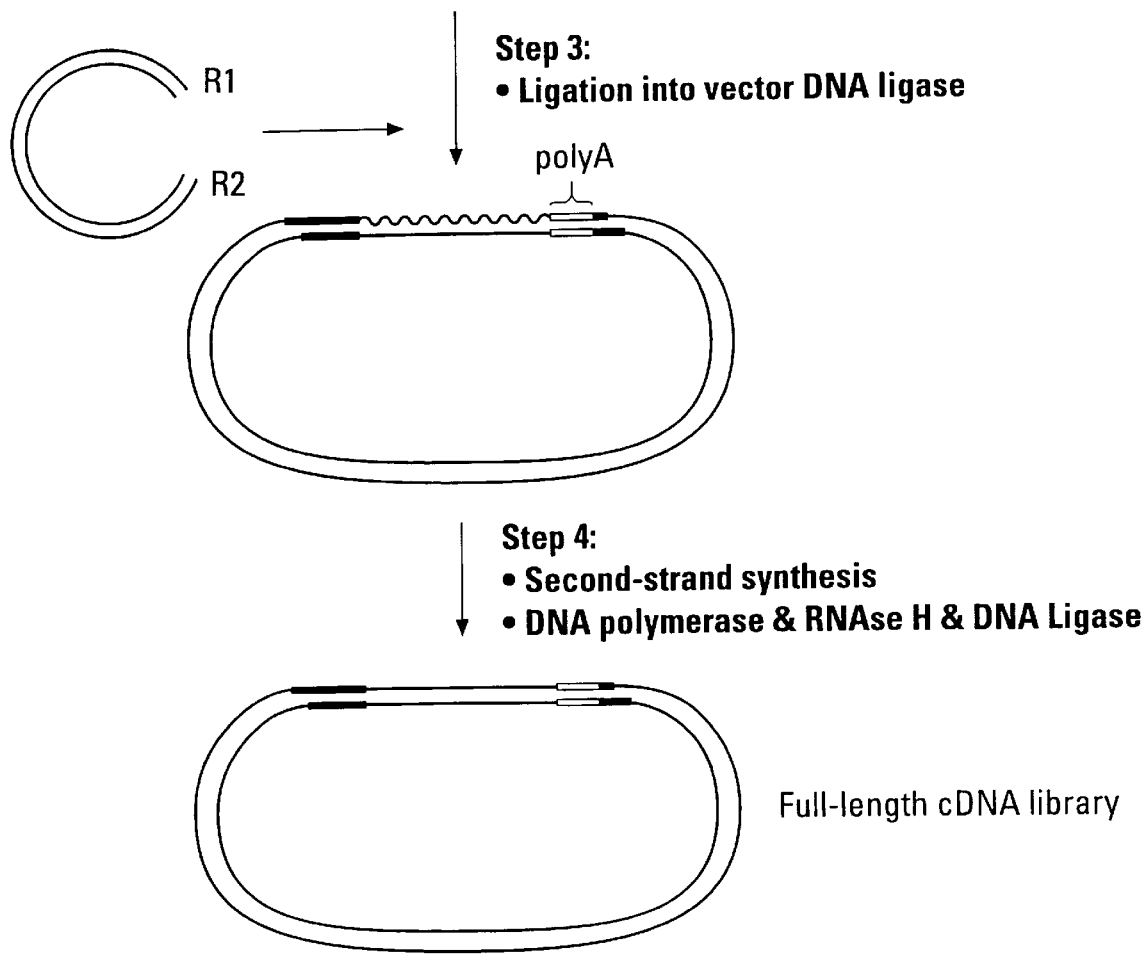

CAPswitch Full-Length cDNA Library Construction Using PRE Adaptor-Primer Strategy CAPswitch technology can be also effectively be combined with standard, conventional (non PCR-based) technologies well known in the art. As a result, conventional procedures can be significantly simplified, and a full-length cDNA rather than a cDNA fragment library will be generated. In this example, as a starting material for cDNA synthesis, we used poly(A)+RNA The flow chart in FIG. 4 illustrates the main step of CAPswitch full-length cDNA library construction technology mainly based on the conventional PRE adaptor-primer procedure described by Coleclough et al., (1985). It will be apparent to those skilled in the art that choice of enzymes possessing similar enzymatic activities, structure of CDS primer (PRE adaptor primer), CAPswitch oligonucleotide and vector, and choice of restriction sites used for cloning, as shown in FIG. 4, can be varied without changing the efficiency of the subject procedure. One modification in the procedure can be to first carry out the second-strand synthesis (step 3) followed by restriction digestion (step 2), and cloning into a vector (step 4). Another modification can include using adaptor ligation procedure described in Example 2 instead of restriction digestion (step 2). Use of the vector primer instead of the PRE adaptor-primer for the first-strand cDNA synthesis (step 1) can also be employed. In this case, the vector primer can have an oligo d(T) sequence at one end to initiate first-strand synthesis and a CAPswitch oligonucleotide sequence at the other end to provide automatic template switching after completion of full-length first-strand cDNA synthesis. Any such variations in the preferred protocol which use methods and materials of the subject invention are within the scope of the invention.

Step 1. Generation of full-length mRNA: cDNA hybrid.

10 pmol of cDNA synthesis primer (CDS3):

5'-d(TCTAGAATTCTCGAGGCGGCCGC(T)$_{30}$VN)-3' (SEQ ID NO. 16)

3'-d(AGATCTTAAGAGCTCCGCCGGCG)-3' (SEQ ID NO. 17)

(where V=G or A or C; N=G or A or T or C), and 10 pmol of CAPswitch oligonucleotide (CSO3):

5'-d(TGCTGCGAGAAGACGACAGAATTCGG)r(GGG)-3' (SEQ ID NO. 18)

were annealed to 5 µg of human skeletal muscle poly(A)+ RNA (CLONTECH Laboratories, Inc.), in a volume of 12.5 µl of deionized water, by heating the mixture for 2 minutes at 70° C., followed by cooling on ice for 2 minutes. First-strand cDNA synthesis-template switching was then initiated by mixing the annealed primer-RNA with 1000 units of M-MLV RNase H- reverse transcriptase (SuperScript II reverse transcriptase, Life Technologies) in a final volume of 25 µl, containing 50 mM Tris-HCl (pH 8.3 at 22° C.); 75 mM KCl; 6 mM MgCl$_2$; 1 mM DTT; and 1 mM each of dATP, dGTP, dCTP, and dTTP. The first-strand cDNA synthesis-template switching reaction was incubated at 42° C. for 1.5 hours in an air incubator and stopped by addition of 75 µl of 150 µg/ml glycogen, 10 mM EDTA The mRNA:cDNA hybrid was extracted once with phenol/chloroform/isoamyl alcohol (25:24:1, vol/vol), once with chloroform/isoamyl alcohol (24:1, vol/vol), and then precipitated by addition of a half volume of 4 M ammonium acetate (about 40 µl) and 3.7 volumes of 95% ethanol (about 300 µl). After vortexing, the tube was immediately centrifuged at 14,000 r.p.m. in a microcentrifuge for 20 minutes. The pellet was washed with 80% ethanol without vortexing, centrifuged as above for 10 minutes, air dried, and dissolved in 50 µl of deionized water.

Step 2. Restriction digestion.

mRNA:cDNA hybrid generated at step 1 was digested for nondirectional cloning by EcoRI restriction endonuclease (EcoRI and NotI or EcoRI and XhoI for directional cloning) for 1 hour at 37° C. in 100 ml of reaction mixture, containing 50 mM Tris-HCl (pH 7.5), 100 mM NaCl, 10 mM MgCl$_2$, 1 mM DTT, and 50 units of EcoRI restriction endonuclease (New England BioLabs). The reaction was then stopped by addition of 5 µl of 2 mg/ml glycogen, 0.2 M EDTA. The mRNA:cDNA hybrid with EcoRI ends was extracted once with phenol/chloroform/isoamyl alcohol (25:24:1, vol/vol), once with chloroform/isoamyl alcohol (24:1, vol/vol), and then precipitated by addition of a half volume of 4 M ammonium acetate (about 40 µl) and 3.7 volumes of 95% ethanol (about 300 µl). After vortexing, the tube was immediately centrifuged at 14,000 r.p.m. in a microcentrifuge for 20 minutes. The pellet was washed with 80% ethanol without vortexing, centrifuged as above for 10 minutes, air dried, and dissolved in 5 µl of deionized water.

Step 3. Ligation into vector.

The EcoRI-digested mRNA:cDNA hybrid was then ligated to the λgt11 EcoRI vector arm (CLONTECH Laboratories, Inc.) overnight at 16° C. under the following conditions: 5 µl of mRNA:cDNA hybrid solution, 50 mM Tris-HCl (pH 7.8 at 22° C.), 10 mM MgCl$_2$, 1 mM DTT, 1 mM ATP, 5% polyethylene glycol (M.W. 8,000), 2.5 µg of λgt11 EcoRI arms, and 2.5 units of T4 DNA ligase (Life Technologies) in a total volume of 20 µl.

Step 4. Second-strand cDNA synthesis.

Second-strand cDNA synthesis was carried out in a total volume of 100 µl, containing 20 µl of the vector-ligated mRNA:cDNA hybrid, 20 mM Tris-HCl (pH 7.5 at 22° C.), 100 mM KCl, 10 mM (NH$_4$)$_2$SO$_4$, 5 mM MgCl$_2$, 0.15 mM β-NAD, 50 µg/ml BSA, 300 units/ml *E. coli* DNA polymerase I, 12 units/ml *E. coli* RNase H, and 60 units/ml *E. coli* DNA ligase. The reaction mixture was incubated at 16° C. for 1.5 hours and stopped by addition of 4 µl of 2 mg/ml glycogen, 0.2 M EDTA The ds cDNA was extracted once with phenol/chloroform/isoamyl alcohol (25:24:1, vol/vol), once with chloroform/isoamyl alcohol (24:1, vol/vol), and then precipitated by addition of a half volume of 4 M ammonium acetate (about 35 µl) and 3.7 volumes of 95% ethanol (about 260 µl). After vortexing, the tube was immediately centrifuged at 14,000 r.p.m. in a microcentrifuge for 20 minutes. The pellet was washed with 80% ethanol without vortexing, centrifuged as above for 10 minutes, air dried, and dissolved in 10 µl of deionized water.

The full-length cDNA library was then packaged using standard protocol described in the laboratory manual by Sambrook et al. (1989). In order to confirm the quality of the library generated by the methods and materials of the present invention, we carried out the same quality control experiments as in Example 2 for the PCR-based technology. The size distribution and high efficiency cloning of full-length cDNAs library were similar for both libraries.

These data show that the methods and compositions of the present invention can be used for cDNA library construction based on PRE adaptor-primer strategy to generate high quality cDNA libraries with a very high level of full-length cDNA clones.

EXAMPLE 4

Preferred Method for Amplification ds cDNA using CAPswitch technology and Using this ds cDNA in cDNA Subtraction The methods and materials of the subject invention were also used for producing high-quality cDNA from nanograms of total or poly A+ RNA. The flow chart in FIG. 1 (step 1 and 2) shows the main steps of this procedure. It will be apparent to those skilled in the art that some modification in the preferred protocol, such as structure of CDS primer, CAPswitch oligonucleotide, time of addition different reaction component can be varied without changing the efficiency of the whole procedure.

In one embodiment of the subject of invention the ds cDNA amplified by methods and materials of the present invention has been used in combination with cDNA subtraction technology. When total RNA is used for cDNA synthesis by conventional methods, ribosomal RNA is transcribed along with poly A+ RNA fraction, even if synthesis is oligo(dT)-primed. If this cDNA is used for cDNA subtraction procedure, the excess of ribosomal RNA, impurities of genomic DNA and low concentration of cDNA corresponding to the poly A+RNA fraction results in inefficient subtractive hybridization. However, cDNA generated using methods and materials of the present invention can be directly used for subtractive hybridization procedure—even if total RNA was used as starting material. In a preferred sub-embodiment, tester and driver ds cDNA amplified by methods and materials of the present invention was used in combination with Suppression Subtractive Hybridization technology (Chenchik et al., U.S. Pat. No. 5,565,340). Other methods of subtractive hybridization, described for example, by Wigler et al. (U.S. Pat. No. 5,436,142); Hampson et al. (Nucl. Acids Res. 20:2899 (1992)); Yang et al. (Anal. Biochem. 237:109–114(1996)); Balzer et al. (Nucl. Acids Res. 22:2853–2854(1994)), and others, can be employed using ss or ds cDNA corresponding tester and/or driver and amplified by according to the methods of the present invention.

Step 1. First-strand synthesis—template switching.

10 pmol of cDNA synthesis primer (oligo d(T) primer) CDS3:

5'-d(AAGCAGTGGTAACAACGCAGAGTAC(T)30-3' (SEQ ID NO.67), and 10 pmol of CAPswitch oligonucleotide (Na1smG3):

5'-d(AAGCAGTGGTAACAACGCAGAGTACGC)r (GGG)-3' (SEQ ID NO.68), were annealed in two separate test tubes to 1 mg of each tester and driver Total RNA (CLONTECH Laboratories, Inc.), in a volume of 5 ml of deionized water, by heating the mixture for 2 min at 70° C., followed by cooling on ice for 2 min. First-strand cDNA synthesis was then initiated by mixing the annealed primer-RNA with 200 units of M-MLV RNAse H- reverse transcriptase (SuperScript II reverse transcriptase, Life Technologies) in a final volume of 10 ml, containing 50 mM Tris-HCl (pH 8.3 at 22° C.), 75 mM KCl, 6 mM MgCl2, 1 mM DTT, 1 mM of each dATP, dGTP, dCTP and dTTP. The first-strand cDNA synthesis-template switching reaction was incubated at 42° C. for 1.5 hr in an air incubator, then diluted by adding the 40 ml of TE buffer (10 mM Tris [pH 7.6], 1 mM EDTA) and heated at 72° C. for 7 min.

Step 2. cDNA Amplification

PCR amplification of full-length cDNA was performed using the Advantage KlenTaq Polymerase Mix (CLONTECH Laboratories, Inc.). Amplification was conducted in a 100-ml volume containing 5 ml of diluted first-strand cDNA, 40 mM Tricine-KOH (pH 9.2 at 22° C.), 3.5 mM Mg(OAc)2, 10 mM KOAc, 75 mg/ml BSA, 200 mM of each dATP, dGTP, dCTP and dTTP, 0.2 mM of PCR primer (Na1sm):

5'-AAGCAGTGGTAACAACGCAGAGT-3' (SEQ ID NO.69)

and 2 ml of KlenTaq Polymerase mix. Temperature parameters of the PCR reactions were as follows: 1 min at 95° C. followed by 17–19 cycles of 95° C. for 15 sec and 68° C. for 5 min; followed by a 10-min final extension at 68° C. PCR products were examined on 1.2% agarose/EtBr gels in 1× TAE buffer. As a DNA size marker we used a 1 Kb DNA Ladder (Life Technologies). Terminate reaction by adding 2 ml of 0.5 M EDTA.

Step 3. cDNA purification.

To tester and driver PCR product combined each from two reaction tubes, add an equal volume of phenol:choloroform:isoamyl alcohol (25:24:1). Vortex thoroughly. Centrifuge the tubes at 14,000 rpm for 10 min to separate the phases. Remove the top (aqueous) layer and place it in a clean 1.5-ml tube. Add 700 ml of n-butanol and vortex the mix thoroughly. Butanol extraction allows you to concentrate PCR product to a volume of 40–70 ml. Centrifuge the solution at room temperature at 14,000 rpm for 1 min. Remove and discard the upper (n-butanol organic) phase. If you do not end up with a volume of 40–70 ml, repeat butanol extraction step with the same volume of n-butanol. Invert a 0.75 ml CHROMA SPIN-1000 (CLONTECH Laboratories, Inc.) column several times to completely resuspend the gel matrix. Remove the top cap from the column, and then remove the bottom cap. Place the column into a 1.5-ml centrifuge tube or a 17×100 mm tube. Discard any column buffer that immediately collects in the tube and add 1.5 ml of 1× TNE buffer (10 mM Tris-HCl (pH 8.0), 10 mM NaCl, 0.1 mM EDTA). Let the buffer drain through the column by gravity flow until you can see the surface of the gel beads in the column matrix. Discard the collected buffer and proceed with purification. Carefully and slowly apply the sample to the center of the gel beds flat surface. Do not allow any sample to flow along the inner wall of the column. Apply 25 ml of 1× TNE buffer and allow the buffer to completely drain out of the column. Apply 150 ml of 1× TNE buffer and allow the buffer to completely drain out of the column. Transfer column to a clean 1.5-ml microcentrifuge tube. Apply 320 ml of 1× TNE buffer and collect this as your purified cDNA fraction. To confirm that your PCR product is present in the purified cDNA fraction, perform the agarose/EtBr gel analysis as described in Step 2.

Step 4. cDNA Subtraction.

Perform an Rsa I digestion and cDNA subtraction as described in details by Chenchik et al. (U.S. Pat. No. 5,565,340).

It should be understood that the examples and embodiments described herein are for illustrative purposes only and that various modifications or changes in light thereof will be suggested to persons skilled in the art and are to be included within the spirit and purview of this application and the scope of the appended claims.

TABLE 1

| Designation and SEQ ID NO. | Sequence Information |
|---|---|
| CzR1 (SEQ ID NO. 1) | 5'- d(TGTAGCGTGAAGACGACAGAA)r(N)$_{12}$ - 3' |
| CzR2 (SEQ ID NO. 2) | 5'- d(TGTAGCGTGAAGACGACAGAA(N)$_{11}$)r(N)$_1$ - 3' |
| CzR3 (SEQ ID NO. 3) | 5'- d(TGTAGCGTGAAGACGACAGAA(N)$_{11}$) - 3' |
| CzR4 (SEQ ID NO. 4) | 5'- d(TGTAGCGTGAAGACGACAGAAGGATG(N)$_9$)r(N)$_1$ - 3' |
| Na21-N4 (SEQ ID NO. 5) | 5'- d(TGTAGCGTGAAGACGACAGAA)r(N)$_4$ - 3' |
| Na21-N8 (SEQ ID NO. 6) | 5'- d(TGTAGCGTGAAGACGACAGAA)r(N)$_8$ - 3' |
| NA21-N12 (SEQ ID NO. 7) | 5'- d(TGTAGCGTGAAGACGACAGAA)r(N)$_{16}$ - 3' |
| CDS1 (SEQ ID NO. 8) | 5'-d(TCTAGAATTCAGCGGCCGC(T)$_{30}$VN) - 3' |
| CSO1 (SEQ ID NO. 9) | 5'-d(CTAATACGACTCACTATAGGGC)r(GGGp)-3' |
| ACT1 (SEQ ID NO. 10) | 5' -ACTCGTCATACTCCTGCTTGCTGATCCACATCTGC - 3' |
| TFR1 (SEQ ID NO. 11) | 5' - GTCAATGTCCCAAACGTCACCAGAGA - 3' |
| CSP1 (SEQ ID NO. 12) | 5'- d(CTAATACGACTCACTATAGGGC)- 3' |
| CSO2 (SEQ ID NO. 13) | 5'-d(CTAATACGACTCACTATAGGGC)r(GGG)-3' |
| Ad1 (SEQ ID NO. 14) | 5' - d(AATTCGCGGCCGCGTCGAC) - 3' |
| Complementary strand to Ad1 (SEQ ID NO. 15) | 3' - d(GCGCCGGCGCAGCTGp) - 5' |
| CDS2 (SEQ ID NO. 16) | 5'- d(TCTAGAATTCTCGAGGCGGCCGC(T)$_{30}$VN) - 3' |
| Complementary strand to CDS2 | 3'- d(AGATCTTAAGAGCTCCGCCGGCG) - 3' |

TABLE 1-continued

| Designation and SEQ ID NO. | Sequence Information |
|---|---|
| (SEQ ID NO. 17) | |
| CS03 (SEQ ID NO. 18) | 5'-d(TGCTGCGAGAAGACGACAGAATTCGG)r(GGG)-3' |

Additional CAPswitch oligonucleotides

| | |
|---|---|
| Na21-G (SEQ ID NO. 19) | 5'- d(TGTAGCGTGAAGACGACAGAA)r(G) - 3' |
| Na21-G3 (SEQ ID NO. 20) | 5'- d(TGTAGCGTGAAGACGACAGAA)r(GGG) - 3' |
| Na21-N4G3 (SEQ ID NO. 21) | 5'- d(TGTAGCGTGAAGACGACAGAA)r($N_4G_3$) - 3' |
| Na21-GCGGCN4G3 (SEQ ID NO. 22) | 5'- d(TGTAGCGTGAAGACGACAGAA)r($GCGGCN_4G_3$) - 3' |
| Na21-GTAAG3 (SEQ ID NO. 23) | 5'- d(TGTAGCGTGAAGACGACAGAA)r($GTAAG_3$) - 3' |
| Na21-GATTG3 (SEQ ID NO. 24) | 5'- d(TGTAGCGTGAAGACGACAGAA)r($GATTG_3$) - 3' |
| Na21-TGTTG3 (SEQ ID NO. 25) | 5'- d(TGTAGCGTGAAGACGACAGAA)r($TGTTG_3$) - 3' |
| Na21-CTAAG3 (SEQ ID NO. 26) | 5'- d(TGTAGCGTGAAGACGACAGAA)r($CTAAG_3$) - 3' |
| Na21-GGTAG3 (SEQ ID NO. 27) | 5'- d(TGTAGCGTGAAGACGACAGAA)r($GGTAG_3$) - 3' |
| Na21-G2p (SEQ ID NO. 28) | 5'- d(TGTAGCGTGAAGACGACAGAA)r(GGp) - 3' |
| Na21-G3p (SEQ ID NO. 29) | 5'- d(TGTAGCGTGAAGACGACAGAA)r(GGGp) - 3' |
| Na21-G5p (SEQ ID NO. 30) | 5'- d(TGTAGCGTGAAGACGACAGAA)r(GGGGGp) - 3' |
| Na21N-g3 (SEQ ID NO. 31) | 5'- d(TGATGCGAGTAGACGACAGAA)r(GGG) - 3' |
| Na21N-G3p (SEQ ID NO. 32) | 5'- d(TGATGCGAGTAGACGACAGAA)r(GGGp) - 3' |
| Na21N-G3p (SEQ ID NO. 33) | 5'- d(TGATGCGAGTAGACGACAGA)r(GGGp) - 3' |
| Na21B-G3p (SEQ ID NO. 34) | 5'- d(TACGATGCGAGTAGACGACAGAA)r(GGGp) - 3' |
| Na22-G3 (SEQ ID NO. 35) | 5'- d(TGCTGCGAGAAGACGACAGAA)r(GGG) - 3' |
| Na22-G3p (SEQ ID NO. 36) | 5'- d(TGCTGCGAGAAGACGACAGAA)r(GGGp) - 3' |
| Na22M-G3 (SEQ ID NO. 37) | 5'- d(TTGCTGGCAGAAGACGACAGA)r(GGG) - 3' |
| T7-G (SEQ ID NO. 38) | 5'- d(CTAATACGACTCACTATAGGGC)r(G) - 3' |
| T7-G2 (SEQ ID NO. 39) | 5'- d(CTAATACGACTCACTATAGGGC)r(GG) - 3' |
| T7-G3 (SEQ ID NO. 40) | 5'- d(CTAATACGACTCACTATAGGGC)r(GGG) - 3' |
| T7-G5 (SEQ ID NO. 41) | 5'- d(CTAATACGACTCACTATAGGGC)r(GGGGG) - 3' |

TABLE 1-continued

| Designation and SEQ ID NO. | Sequence Information |
|---|---|
| T7-Gp (SEQ ID NO. 42) | 5'- d(CTAATACGACTCACTATAGGGC)r(Gp) - 3' |
| T7-G2p (SEQ ID NO. 43) | 5'- d(CTAATACGACTCACTATAGGGC)r(GGp) - 3' |
| T7-G3p (SEQ ID NO. 44) | 5'- d(CTAATACGACTCACTATAGGGC)r(GGGp) - 3' |
| T7-G5p (SEQ ID NO. 45) | 5'- d(CTAATACGACTCACTATAGGGC)r(GGGGGp) - 3' |
| T7-GCG (SEQ ID NO. 46) | 5'- d(CTAATACGACTCACTATAGGGC)r(GCG) - 3' |
| T7-GCG2 (SEQ ID NO. 47) | 5'- d(CTAATACGACTCACTATAGGGC)r(GCGG) - 3' |
| T7-CG (SEQ ID NO. 48) | 5'- d(CTAATACGACTCACTATAGGGC)r(CG) - 3' |
| T7-DG (SEQ ID NO. 49) | 5'- d(CTAATACGACTCACTATA)r(GGGCG) - 3' |
| T7-N9G3 (SEQ ID NO. 50) | 5'- d(CTAATACGACTCACTATAGGGC)r($N_9$GGG) - 3' |
| T7-GCG3 (SEQ ID NO. 51) | 5'- d(CTAATACGACTCACTATAGGGC)r(GCGGG) - 3' |
| T7-SUP1 (SEQ ID NO. 52) | 5'-d(CTAATACGACTCACTATAGGGCGCGGCCGCCCGGG)r(GCG3)-3' |
| T7-SUP2 (SEQ ID NO. 53) | 5 -d(CTAATACGACTCACTATAGGGCACGCGTGGTCGACGGCCCGG)r(GCG3)-3' |
| T7-G3-NH2 (SEQ ID NO. 54) | 5'-d(CTAATACGACTCACTATAGGGC)r(GGG-$NH_2$) - 3' (where NH2 is an amino group at the position of the ribose residue) |
| T7-G3-BIO (SEQ ID NO. 55) | 5'-d(CTAATACGACTCACTATAGGGC)r(GGG-BIO) - 3' (where BIO is a biotin group at the position of the ribose residue) |
| T7-G3-GLY (SEQ ID NO. 55) | 5'-d(CTAATACGACTCACTATAGGGC)r(GGG-GLY) - 3' (where GLY is a glycerol group at the position of the ribose residue) |
| T7-GAG3p (SEQ ID NO. 57) | 5'-d(CTAATACGACTCACTATAGGGC)r(GAGGGp) - 3' |
| T7-GTG3p (SEQ ID NO. 58) | 5'-d(CTAATACGACTCACTATAGGGC)r(GTGGGp) - 3' |
| T7-GGAG2p (SEQ ID NO. 59) | 5'-d(CTAATACGACTCACTATAGGGC)r(GGAGGp) - 3' |
| T7-GGTG2p (SEQ ID NO. 60) | 5'-d(CTAATACGACTCACTATAGGGC)r(GGTGGp) - 3' |
| T7-GACG2p (SEQ ID NO. 61) | 5'-d(CTAATACGACTCACTATAGGGC)r(GACGGp) - 3' |
| T7-GATG2p (SEQ ID NO. 62) | 5'-d(CTAATACGACTCACTATAGGGC)r(GATGGp) - 3' |
| T7-GTTG2p (SEQ ID NO. 63) | 5'-d(CTAATACGACTCACTATAGGGC)r(GTTGGp) - 3' |
| T7-GAGTGp1 (SEQ ID NO. 64) | 5'-d(CTAATACGACTCACTATAGGGC)r(GAGTGp) - 3' |
| T7M-GGAG3p (SEQ ID NO. 65) | 5'-d(TCCTAATACGACTCACTATA)r(GGAGGGp) - 3' |
| T7-GAG3p | 5'-d(CTAATACGACTCACTATAGGGC)r(GGAGGp) - 3' |

TABLE 1-continued

| Designation and SEQ ID NO. | Sequence Information |
|---|---|
| (SEQ ID NO. 66) | |
| CDS3 (SEQ ID NO. 67) | 5'-d(AAGCAGTGGTAACAACGCAGAGTAC(T)$_{30}$) - 3' |
| Na1smG3 (SEQ ID NO. 68) | 5'-d(AAGCAGTGGTAACAACGCAGAGTACGC)r(GGG) - 3' |
| Na1sm (SEQ ID NO. 69) | 5'- d(AAGCAGTGGTAACAACGCAGAGT) - 3' |
| Na21-Bio (SEQ ID NO. 70) | 5'- d(Bio-TGTAGCGTGAAGACGACAGAA) - 3' |
| T7N (SEQ ID NO. 71) | 5'- d(CTAATACGACTCACTATAGGGC) - 3' |
| EXT7 (SEQ ID NO. 72) | 5'- d(TGCCATCCTAATACGACTCACTA) - 3' |
| T7MFok (SEQ ID NO. 73) | 5'- d(CTAATACGACTCACGGATGGGC) - 3' |
| Na21N (SEQ ID NO. 74) | 5'- d(TGATGCGAGTAGACGACAGAA) - 3' |
| Na22 (SEQ ID NO. 75) | 5'- d(TGCTGCGAGAAGACGACAGAA)- 3' |
| Na22M (SEQ ID NO. 76) | 5'- d(TTGCTGGCAGAAGACGACAGA) - 3' |
| Na21B (SEQ ID NO. 77) | 5'- d(TACGATGCGAGTAGCGACAGAA) - 3' |
| Fr1 (SEQ ID NO. 78) | 5'- d(TGACCAGTGAGCAGAGTGACGA) - 3' |
| T3 (SEQ ID NO. 79) | 5'- d(CCATCCAATTAACCCTCACTAAAGGGC) - 3' |
| Na1M (SEQ ID NO. 80) | 5'- d(AAGCAGAGGCAACAACGCAGA) - 3' |
| T7M2 (SEQ ID NO. 81) | 5'- d(ACAAGACGAAGCACAAGAGGGC) - 3' |
| Na1M (SEQ ID NO. 82) | 5'- d(AAGCAGAGGCAACAACGCAGA) - 3' |
| T7T (SEQ ID NO. 83) | 5'- d(TTCCGCTTGTCTGCTGGGC) - 3' |
| RT7AS4 (SEQ ID NO. 84) | 5'- d(CGTGCGGCCGCTTCGAG-NH$_2$) - 3' |
| 3BPAS (SEQ ID NO. 85) | 5'- d(GAGCGGCCGCACGAG-NH$_2$) - 3' |
| RT7-G3 (SEQ ID NO. 86) | 5'- r(CTAATACGACTCACTATAGGGCGGG) - 3' |
| RT7Fok-G3 (SEQ ID NO. 87) | 5'- r(CTAATACGACTCACTATAGGGCGGATGGG) - 3' |
| RT7In3 (SEQ ID NO. 88) | 5'- r(CTAATACGACTCACTATAGGGC)d(III) - 3' |
| RT7Un3 (SEQ ID NO. 89) | 5'- r(CTAATACGACTCACTATAGGGC)d(UUU) - 3' |
| Na1Sup2M (SEQ ID NO. 90) | 5'-(AAGCAGAGGCAACAACGCAGAGAGGGCAGCAGGCAGC)r(GGG)-3' |
| RT7NS2M (SEQ ID NO. 91) | 5'-(AGACGAAGCACAAGAGGGCACGAGCGGCCGCACGGCG)r(GGG)-3' |

TABLE 1-continued

| Designation and SEQ ID NO. | Sequence Information |
| --- | --- |
| RT7NSM-F (SEQ ID NO. 92) | 5'-(ATACGACTCACTATAGGGCTCGAGCGGCCGCACGGCG)r(GGG-F)-3' |
| Na1SMG3-F (SEQ ID NO. 93) | 5'-(AAGCAGAGTGCTAACAACGCAGAGTACGC)r(GGG-F)-3' |
| T7-G3F (SEQ ID NO. 94) | 5'-(ATACGACTCACTATAGGGC)r(GGG-F)-3' |
| T7-GCG3F (SEQ ID NO. 95) | 5'-(ATACGACTCACTATAGGGC)r(GCGGG-F)-3' |
| T3-G3 (SEQ ID NO. 96) | 5'-(ATTAACCCTCACTAAAGGGC)r(GGG)-3' |
| T3-NSM (SEQ ID NO. 97) | 5'-(ATTAACCCTCACTAAAGGGCTCGAGCGGCCGCACGGCG)r(GGG)-3' |
| Na1SM-GCG3 (SEQ ID NO. 98) | 5'd(AAGCAGTGGTATCAACGCAGAGTAC)r(GCGGG) - 3' |
| Na1-GCG3 (SEQ ID NO. 99) | 5'-d(AAGCAGTGGTAACAACGCAGAGT)r(GCGGG) - 3' |
| Na1Sup1 (SEQ ID NO. 100) | 5'-d(AAGCAGTGGTAACAACGCAGAGTGGGCAGCAGGCA)r(GCGGG)-3' |
| Na1M-G3 (SEQ ID NO. 101) | 5'-d(AAGCAGTGGTATCAACGCAGAGTACGC)r(GGG) - 3' |
| Na1SMG3 (SEQ ID NO. 102) | 5'-d(AAGCAGTGGTAACAACGCAGAGTACGC)r(GGG) - 3' |
| Na1Sup1M (SEQ ID NO. 103) | 5'-d(AAGCAGTGGTAACAACGCAGAGTGGGCAGCAGCCAGC)r(GGG)-3' |
| RT7NSM (SEQ ID NO. 104) | 5'-d(ATACGACTCACTATAGGGCTCGAGCGGCCGCACGGCG)r(GGG)-3' |
| RT7NS2 (SEQ ID NO. 105) | 5'-d(ATACGACTCACTATAGGGCTCGAGCGGCCGCCCGGGCAG)r(GGG) - 3' |
| RT7Sup4 (SEQ ID NO. 106) | 5'-d(ATACGACTCACTATAGGGCTCGGTCGGGCAGGCACGGCG)r(GGG) - 3' |
| 3BP-NSMT (SEQ ID NO. 107) | 5'-d(TTCCGCTTGTCTGCTGGGCTCGTGCGGCCGCTCGGCG)r(GGG)-3' |
| RT7-NS3M (SEQ ID NO. 108) | 5'-d(AGACGAAGCACAAGAGGGCACGAGCAGCGGCACGGCG)r(GGG)-3' |
| Fr-T30NN (SEQ ID NO. 109) | 5'-d(TGACCAGTGAGCAGAGTGACGAGTAC(T)$_{30}$VN)-3' |
| T7-T30NN (SEQ ID NO. 110) | 5'-d(CCATCCTAATACGACTCACTATAGGGC(T)$_{30}$VN) -3' |
| Bio-T7-T30NN (SEQ ID NO. 111) | 5'-d(Bio-AATACGACTCACTATAGGGC(T)$_{30}$VN) -3' |
| (SEQ ID NO. 112) | 5'-d(TGCTGCGGAAGACGACAGAA)r(GGG)-3' |
| (SEQ ID NO. 113) | 5'-d(TGCTGCGGAAGACGACAGAA)-3' |
| (SEQ ID NO. 114) | 5'-d(AATTCGAGCGGCCGC(T)$_{30}$VN)-3' |

V = G or A or C
N = G or A or T or C
p is 3'-phosphate group
NH2 is an amino group
BIO is a biotin group
GLY is a glycerol group
I is inosine
U is deoxyribofuranosyl-5-nitroindole phosphate
F is a fluoro group at the 3' position of the ribose residue

References

Kimmel, A. R., S. L. Berger (1987) "Preparation of cDNA and the generation of cDNA libraries: Overview," *Meth. Enzymol.* 152:307–316.

Sonenberg, N., I. Edery, M. Altmann, U.S. Pat. No. 5,219,989, issued Jun. 15, 1993.

Wu, R. ed. (1987) *Methods in Enzymology*, vol. 152, Academic Press, pp. 307–389.

Gubler, U., B. J. Hoffmanm (1983) *Gene* 25:253–269.

Okayma and Berg (1982) *Mol. Cell. Biol.* 2:161–170.

Pruitt, S. C., International Patent. Appl. No. 89110816.9.

Edery, A., L. L. Chu, N. Sonenberg, J. Pelletier (1995) *Mol. Cell Biol.* 15:3363–3371.

Maruyama, K., S. Sugano (1994) *Gene* 138:171–174.

Fromomt-Racine, M., E. B. Pictet, T. Grande (1993) *Nucl. Acids Res.* 21:1683–1684.

Kato, S., S. Sekine, International Patent Publ. No. 0 625 572 A1, Appl. No. 93921061.3 of 22.09.93; Intern. Appl. No. PCT/JP93/01359.

Kato, S. (1994) *Gene* 150:243–250.

Telesnitsky, A., S. Goff (1993) *Reverse Transcriptase* (Skalka, A. M. and Goff, S. P., eds), Cold Spring Harbor Laboratory Press, Cold Spring Harbor, N.Y., pp. 49–83.

Kenan, D. J., D. E. Tsai, J. D. Keene (1994) *Trends Biochem. Sci.* 19:57–64.

Coleclough and Erlitz (1985) *Gene* 34:305–314.

Li, W. -B., C. Gruber, J. Jessee, J. -J. Lin, International Patent. Appl. No. PCT/US94/09038, Publ. No. WO 95/104745; filing date: 9 Aug. 1994; Publ. date: 16 Feb., 1994.

Cheng, S., International Patent Appl. No. 95102141.9; Publ. No. 0 669 401 A2.

Barnes, W. M., U.S. Pat. No. 5,436,149 issued Jul. 25, 1995.

Frohman, M. A., M. K. Dush, G. R. Martin (1988) *Proc. Natl. Acad. Sci. USA* 85:8998–9002.

Sambrook, J., E. F. Fritsch, T. Maniatis (1989) *Molecular Cloning: A Laboratory Manual*, Cold Spring Harbor Laboratory Press, Cold Spring Harbor, N.Y.

Goff, S. P., Tanese, N. and Roth, M. J. "Expression of enzymatically active reverse transcriptase" U.S. Pat. No. 4,943,531; Issued Jul. 24, 1990.

Kotewics, M. L. and Gerard, G. F. "Cloned genes encoding reverse transcriptase lacking RNASE H activity" U.S. Pat. No. 5,405,776 Issued Apr. 11, 1995.

Gelfand, D. H. "Reverse transcription with thermostable DNA polymerases—high temperature reverse transcription" U.S. Pat. No. 5,322,770 Issued Jun. 21, 1994.

Li, W. -B., Gruber, C. E., Jessee, J. A. and Lin, J. -J. "Method of nucleic acid sequence selection" U.S. Pat. No. 5,500,356 Issued Mar. 19, 1996.

Ludwig, L. B. Method for preselting recombinant clones containing a specific nucleic acid sequence and subsequent transformation with preselected clones. U.S. Pat. No. 5,484,702 Issued Jan. 16, 1996.

Chenchik, A., Diatchenko, L., Siebert, P., Lukianov, S., Lukianov, K., Gurskaya, N., Tarabykin, V. and Sverdlov, E. Method for Suppressing DNA fragment Amplification During PCR. U.S. Pat. No. 5,565,340. Date of Patent: Oct. 15, 1996.

Wigler, M. and Lisitsyn, N. Methods for Producing Probes Capable of Distingushing Variant Genomic Sequences. U.S. Pat. No. 5,436,142. Date of Patent: Jul. 25, 1995.

Hampson, I. N., Pope. L., Cowling, G. J. and Dexter T. M. (1992) Chemical crosslinking subtraction (CCLS): a new method for the generation of subtractive hybridization probes. Nucl. Acids. Res. 20:2899.

Yang, M. and Sytkowski, A. J. Cloning Differentially Expressed Genes by Linker Capture Subtraction. Anal. Biochem. 237:109–114.

Balzer, H. J. and Baumlein, H. An Improved Gene Expression Screen. Nucl. Acids Res. 22:2853–2854.

Keller, G. H. and Manak, M. M. (1993) DNA probes. Background. Applications. Procedures. Second Edition. (Macmillan Publishers Ltd.), Stockton Press, New York.

Rosenberg, M., Debouck, C. and Bergsma, D. Differentially Expressed Genes in Healthy and Diseased Subjects. International Patent No. WO 95/21944. Intl. Publication Date: 17 Aug., 1995.

Radding, C. M., Honigberg, S. M., Weissman, S., Rigas, B., Welcher, A. A. and Ward, D. C. RecA Nucleoprotein Filament and Methods, U.S. Pat. No. 4,888,274. Date of Patent: Dec. 19, 1989.

---

We claim:

1. A method for preparing DNA that is complementary to an RNA molecule and a template switching oligonucleotide, said method comprising the steps of:

annealing a cDNA synthesis primer to said RNA molecule and synthesizing a first cDNA strand to form an RNA-cDNA intermediate;

contacting said RNA-cDNA intermediate with a template switching oligonucleotide, wherein said template switching oligonucleotide has at it's 3' end at least one nucleotide which forms a basepair(s) with a nucleotide (s) at a 3' end of said first cDNA strand of said RNA-cDNA intermediate, said template switching oligonucleotide serves as a template for extension of said 3' end of said first cDNA strand, and said template switching oligonucleotide has a pre-selected arbitrary nucleotide sequence at its 5' end and at least one ribonucleotide residue at its 3' end; and extending said 3' end of said first cDNA strand to produce a DNA that is complementary to said RNA molecule and said template switching oligonucleotide.

2. The method according to claim 1, wherein said at least one ribonucleotide residue of said template switching oligonucleotide is riboguanine.

3. The method according to claim 1, wherein said template switching oligonucleotide comprises at least three ribonucleotide residues.

4. The method according to claim 3, wherein at least two of said at least three ribonucleotide residues are riboguanine.

5. The method according to claim 1, further comprising amplifying said DNA strand that is complementary to said RNA molecule and said template switching oligonucleotide using an oligonucleotide primer that comprises a nucleotide sequence comprising at least a portion of said pre-selected nucleotide sequence of said template switching oligonucleotide.

6. The method according to claim 1, wherein said RNA molecule has a 7-methylguanosine CAP structure attached at the 5'-end of said RNA.

7. The method according to claim 1, wherein said template switching oligonucleotide has at least three riboguanine residues at its 3' end.

8. The method according to claim 1, wherein a 3'-OH group of said at least one ribonucleotide comprises a chemical group selected from the group consisting of amino, biotin, phosphate, glycerol and fluoro.

9. The method according to claim 1, wherein said template switching oligonucleotide comprises a protein that binds to a 5' CAP structure of said RNA.

10. The method according to claim 9, wherein said protein is selected from the group consisting of eukaryotic initiation factor 4E and anti-CAP structure antibody.

11. The method according to claim 1, wherein said template switching oligonucleotide is represented by a formula of 5'-$dN_1$-$dN_2$- . . . $dN_m$-$rN_1$-$rN_2$. . . $rN_n$-3', wherein dN represents a deoxyribonucleotide; m represents an integer; rN represents an ribonucleotide at least one of which is GMP and n represents an integer.

12. The method according to claim 1, wherein said template switching oligonucleotide is selected from the group consisting of SEQ ID Nos. 1–7, 9, 13, 18–66, 68, and 84–108.

13. The method according to claim 1, wherein said cDNA synthesis primer comprises a sequence complementary to at least one target RNA.

14. The method according to claim 1, wherein said cDNA synthesis primer comprises a sequence complementary to a poly(A) portion of said RNA.

15. The method according to claim 1, wherein said cDNA synthesis primer is selected from the group consisting of SEQ ID No.8, 16, 67, 109, 110 and 111.

16. The method according to claim 1, wherein said pre-selected arbitrary nucleotide sequence of said template switching oligonucleotide comprises at least one nucleotide with a hapten group, and further comprises the steps of incubating said RNA-cDNA-hapten intermediate with a binding ligand of said hapten group, where said binding ligand is conjugated to a support, under conditions sufficient to permit said hapten to become bound to said binding ligand to produce an intermediate-hapten-ligand complex; washing said intermediate-hapten-ligand complex; and separating said intermediate-hapten from said binding ligand.

17. The method according to claim 1, further comprising the step of incubating said DNA strand that is complementary to said RNA molecule and said template switching oligonucleotide under conditions wherein a second DNA strand complementary to said DNA strand that is complementary to said RNA molecule and said template switching oligonucleotide is synthesized.

18. The method according to claim 1, further comprising the steps of incubating said DNA strand that is complementary to said RNA molecule and said template switching oligonucleotide with at least one primer, wherein said primer comprises a nucleotide sequence comprising at least a portion of said pre-selected arbitrary sequence of said template switching oligonucleotide, and an effective amount of reagents necessary to perform PCR to produce a PCR cocktail, and incubating said PCR cocktail under conditions suitable for generating a full-length double-stranded cDNA.

19. The method according to claim 18, wherein said primer is selected from the group consisting of SEQ ID No. 10, 11, 12, 17, 69, and 70–83.

20. A template switching oligonucleotide having at it's 3' end at least one nucleotide which forms a basepair(s) with a nucleotide(s) at a 3' end of a first cDNA strand of an RNA-cDNA intermediate, wherein said template switching oligonucleotide is capable of serving as a template for extension of said 3' end of said first cDNA strand, and said template switching oligonucleotide has a pre-selected arbitrary nucleotide sequence at its 5' end and at least three ribonucleotide residues at its 3' end.

21. The template switching oligonucleotide of claim 20, wherein at least one of said three ribonucleotide residues is a riboguanine residue.

22. The template switching oligonucleotide of claim 20, wherein said template switching oligonucleotide has a general formula of 5'-$dN_1$-$dN_2$- . . . $dN_m$-$rN_1$-$rN_2$. . . $rN_n$-3', wherein dN represents a deoxyribonucleotide; m represents an integer; rN represents an ribonucleotide at least one of which is GMP and n represents an integer.

23. The template switching oligonucleotide of claim 22, wherein m represents an integer between 10 and 50.

24. The template switching oligonucleotide of claim 22, wherein n represents an integer between 3 and 7.

25. The template switching oligonucleotide of claim 22, wherein an 3'-OH group of said GMP comprises a chemical group selected from the group consisting of amino, biotin, phosphate, glycerol and fluoro.

26. The template switching oligonucleotide of claim 22, wherein said template switching oligonucleotide further comprises a protein capable of binding to a 5' CAP structure of said mRNA.

27. The template switching oligonucleotide of claim 26, wherein said protein is selected from the group consisting of eukaryotic initiation factor 4E and anti-CAP structure antibody.

28. A template switching oligonucleotide selected from the group consisting of SEQ ID Nos. 1–7, 9, 13, 18–66, 68, and 84–108.

29. A kit comprising the template switching oligonucleotide of claim 20.

* * * * *

SEQUENCE LISTING (1) GENERAL INFORMATION:

(iii) NUMBER OF SEQUENCES: 114

(2) INFORMATION FOR SEQ ID NO:1:

(i) SEQUENCE CHARACTERISTICS:
      (A) LENGTH: 33 bases
      (B) TYPE: nucleic acid
      (C) STRANDEDNESS: single
      (D) TOPOLOGY: linear (ii) MOLECULE TYPE: DNA (synthetic)

(xi) SEQUENCE DESCRIPTION: SEQ ID NO:1:

TGTAGCGTGA AGACGACAGA ANNNNNNNNN NNN      33

(2) INFORMATION FOR SEQ ID NO:2:

(i) SEQUENCE CHARACTERISTICS:
      (A) LENGTH: 33 bases (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:2:

TGTAGCGTGA AGACGACAGA ANNNNNNNNN NNN                33

(2) INFORMATION FOR SEQ ID NO:3:

(i) SEQUENCE CHARACTERISTICS:
        (A) LENGTH: 32 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:3:

TGTAGCGTGA AGACGACAGA ANNNNNNNNN NN                 32

(2) INFORMATION FOR SEQ ID NO:4:

(i) SEQUENCE CHARACTERISTICS:
        (A) LENGTH: 36 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:4:

TGTAGCGTGA AGACGACAGA AGGATGNNNN NNNNNN             36

(2) INFORMATION FOR SEQ ID NO:5:

(i) SEQUENCE CHARACTERISTICS:
        (A) LENGTH: 25 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:5:

TGTAGCGTGA AGACGACAGA ANNNN                         25

(2) INFORMATION FOR SEQ ID NO:6:

(i) SEQUENCE CHARACTERISTICS:
        (A) LENGTH: 29 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:6:

TGTAGCGTGA AGACGACAGA ANNNNNNNN                     29

(2) INFORMATION FOR SEQ ID NO:7:

(i) SEQUENCE CHARACTERISTICS:
        (A) LENGTH: 37 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:7:

TGTAGCGTGA AGACGACAGA ANNNNNNNNN NNNNNNN 37

(2) INFORMATION FOR SEQ ID NO:8:

(i) SEQUENCE CHARACTERISTICS:
        (A) LENGTH: 51 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:8:

TCTAGAATTC AGCGGCCGCT TTTTTTTTTT TTTTTTTTTT TTTTTTTTTV N 51

(2) INFORMATION FOR SEQ ID NO:9:

(i) SEQUENCE CHARACTERISTICS:
        (A) LENGTH: 25 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:9:

CTAATACGAC TCACTATAGG GCGGG 25

(2) INFORMATION FOR SEQ ID NO:10:

(i) SEQUENCE CHARACTERISTICS:
        (A) LENGTH: 35 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:10:

ACTCGTCATA CTCCTGCTTG CTGATCCACA TCTGC 35

(2) INFORMATION FOR SEQ ID NO:11:

(i) SEQUENCE CHARACTERISTICS:
        (A) LENGTH: 26 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:11:

GTCAATGTCC CAAACGTCAC CAGAGA 26

(2) INFORMATION FOR SEQ ID NO:12:

(i) SEQUENCE CHARACTERISTICS:
        (A) LENGTH: 22 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:12:

CTAATACGAC TCACTATAGG GC 22

(2) INFORMATION FOR SEQ ID NO:13:

(i) SEQUENCE CHARACTERISTICS:
        (A) LENGTH: 25 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:13:

```
CTAATACGAC TCACTATAGG GCGGG                                   25
```

(2) INFORMATION FOR SEQ ID NO:14:

(i) SEQUENCE CHARACTERISTICS:
        (A) LENGTH: 19 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:14:

```
AATTCGCGGC CGCGTCGAC                                          19
```

(2) INFORMATION FOR SEQ ID NO:15:

(i) SEQUENCE CHARACTERISTICS:
        (A) LENGTH: 15 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:15:

```
GTCGACGCGG CCGCG                                              15
```

(2) INFORMATION FOR SEQ ID NO:16:

(i) SEQUENCE CHARACTERISTICS:
        (A) LENGTH: 55 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:16:

```
TCTAGAATTC TCGAGGCGGC CGCTTTTTTT TTTTTTTTTT TTTTTTTTTT TTTVN   55
```

(2) INFORMATION FOR SEQ ID NO:17:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:17:

```
GCGGCCGCCT CGAGAATTCT AGA                                     23
```

(2) INFORMATION FOR SEQ ID NO:18:

(i) SEQUENCE CHARACTERISTICS:
        (A) LENGTH: 29 bases (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:18:

TGCTGCGAGA AGACGACAGA ATTCGGGGG                                         29

(2) INFORMATION FOR SEQ ID NO:19:

(i) SEQUENCE CHARACTERISTICS:
        (A) LENGTH: 22 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:19:

TGTAGCGTGA AGACGACAGA AG                                                22

(2) INFORMATION FOR SEQ ID NO:20:

(i) SEQUENCE CHARACTERISTICS:
        (A) LENGTH: 24 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:20:

TGTAGCGTGA AGACGACAGA AGGG                                              24

(2) INFORMATION FOR SEQ ID NO:21:

(i) SEQUENCE CHARACTERISTICS:
        (A) LENGTH: 28 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:21:

TGTAGCGTGA AGACGACAGA ANNNNGGG                                          28

(2) INFORMATION FOR SEQ ID NO:22:

(i) SEQUENCE CHARACTERISTICS:
        (A) LENGTH: 33 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:22:

TGTAGCGTGA AGACGACAGA AGCGGCNNNN GGG                                    33

(2) INFORMATION FOR SEQ ID NO:23:

(i) SEQUENCE CHARACTERISTICS:
        (A) LENGTH: 28 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:23:

TGTAGCGTGA AGACGACAGA AGTAAGGG                28

(2) INFORMATION FOR SEQ ID NO:24:

(i) SEQUENCE CHARACTERISTICS:
        (A) LENGTH: 28 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:24:

TGTAGCGTGA AGACGACAGA AGATTGGG                28

(2) INFORMATION FOR SEQ ID NO:25:

(i) SEQUENCE CHARACTERISTICS:
        (A) LENGTH: 28 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:25:

TGTAGCGTGA AGACGACAGA ATGTTGGG                28

(2) INFORMATION FOR SEQ ID NO:26:

(i) SEQUENCE CHARACTERISTICS:
        (A) LENGTH: 28 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:26:

TGTAGCGTGA AGACGACAGA ACTAAGGG                28

(2) INFORMATION FOR SEQ ID NO:27:

(i) SEQUENCE CHARACTERISTICS:
        (A) LENGTH: 28 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:27:

TGTAGCGTGA AGACGACAGA AGGTAGGG                28

(2) INFORMATION FOR SEQ ID NO:28:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:28:

TGTAGCGTGA AGACGACAGA AGG                     23

(2) INFORMATION FOR SEQ ID NO:29:

(i) SEQUENCE CHARACTERISTICS:
        (A) LENGTH: 24 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:29:

TGTAGCGTGA AGACGACAGA AGGG        24

(2) INFORMATION FOR SEQ ID NO:30:

(i) SEQUENCE CHARACTERISTICS:
        (A) LENGTH: 26 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:30:

TGTAGCGTGA AGACGACAGA AGGGGG        26

(2) INFORMATION FOR SEQ ID NO:31:

(i) SEQUENCE CHARACTERISTICS:
        (A) LENGTH: 24 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:31:

TGATGCGAGT AGACGACAGA AGGG        24

(2) INFORMATION FOR SEQ ID NO:32:

(i) SEQUENCE CHARACTERISTICS:
        (A) LENGTH: 24 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:32:

TGATGCGAGT AGACGACAGA AGGG        24

(2) INFORMATION FOR SEQ ID NO:33:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:33:

TGATGCGAGT AGACGACAGA GGG        23

(2) INFORMATION FOR SEQ ID NO:34:

(i) SEQUENCE CHARACTERISTICS:
        (A) LENGTH: 26 bases (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:34:

TACGATGCGA GTAGACGACA GAAGGG                                              26

(2) INFORMATION FOR SEQ ID NO:35:

(i) SEQUENCE CHARACTERISTICS:
            (A) LENGTH: 24 bases
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:35:

TGCTGCGAGA AGACGACAGA AGGG                                                24

(2) INFORMATION FOR SEQ ID NO:36:

(i) SEQUENCE CHARACTERISTICS:
            (A) LENGTH: 24 bases
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:36:

TGCTGCGAGA AGACGACAGA AGGG                                                24

(2) INFORMATION FOR SEQ ID NO:37:

(i) SEQUENCE CHARACTERISTICS:
            (A) LENGTH: 24 bases
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:37:

TTGCTGGCAG AAGACGACAG AGGG                                                24

(2) INFORMATION FOR SEQ ID NO:38:

(i) SEQUENCE CHARACTERISTICS:
            (A) LENGTH: 23 bases
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:38:

CTAATACGAC TCACTATAGG GCG                                                 23

(2) INFORMATION FOR SEQ ID NO:39:

(i) SEQUENCE CHARACTERISTICS:
            (A) LENGTH: 24 bases
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:39:

CTAATACGAC TCACTATAGG GCGG                              24

(2) INFORMATION FOR SEQ ID NO:40:

(i) SEQUENCE CHARACTERISTICS:
        (A) LENGTH: 25 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:40:

CTAATACGAC TCACTATAGG GCGGG                             25

(2) INFORMATION FOR SEQ ID NO:41:

(i) SEQUENCE CHARACTERISTICS:
        (A) LENGTH: 27 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:41:

CTAATACGAC TCACTATAGG GCGGGGG                           27

(2) INFORMATION FOR SEQ ID NO:42:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:42:

CTAATACGAC TCACTATAGG GCG                               23

(2) INFORMATION FOR SEQ ID NO:43:

(i) SEQUENCE CHARACTERISTICS:
        (A) LENGTH: 24 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:43:

CTAATACGAC TCACTATAGG GCGG                              24

(2) INFORMATION FOR SEQ ID NO:44:

(i) SEQUENCE CHARACTERISTICS:
        (A) LENGTH: 25 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:44:

CTAATACGAC TCACTATAGG GCGGG                             25

(2) INFORMATION FOR SEQ ID NO:45:

(i) SEQUENCE CHARACTERISTICS:
        (A) LENGTH: 27 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:45:

CTAATACGAC TCACTATAGG GCGGGGG                                              27

(2) INFORMATION FOR SEQ ID NO:46:

(i) SEQUENCE CHARACTERISTICS:
        (A) LENGTH: 25 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:46:

CTAATACGAC TCACTATAGG GCGCG                                                25

(2) INFORMATION FOR SEQ ID NO:47:

(i) SEQUENCE CHARACTERISTICS:
        (A) LENGTH: 26 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:47:

CTAATACGAC TCACTATAGG GCGCGG                                             26

(2) INFORMATION FOR SEQ ID NO:48:

(i) SEQUENCE CHARACTERISTICS:
        (A) LENGTH: 24 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:48:

CTAATACGAC TCACTATAGG GCCG                                                 24

(2) INFORMATION FOR SEQ ID NO:49:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:49:

CTAATACGAC TCACTATAGG GCG                                                   23

(2) INFORMATION FOR SEQ ID NO:50:

(i) SEQUENCE CHARACTERISTICS:
        (A) LENGTH: 34 bases (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:50:

CTAATACGAC TCACTATAGG GCNNNNNNNN NGGG                                34

(2) INFORMATION FOR SEQ ID NO:51:

(i) SEQUENCE CHARACTERISTICS:
        (A) LENGTH: 27 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:51:

CTAATACGAC TCACTATAGG GCGCGGG                                       27

(2) INFORMATION FOR SEQ ID NO:52:

(i) SEQUENCE CHARACTERISTICS:
        (A) LENGTH: 40 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:52:

CTAATACGAC TCACTATAGG GCGCGGCCGC CCGGGGCGGG                         40

(2) INFORMATION FOR SEQ ID NO:53:

(i) SEQUENCE CHARACTERISTICS:
        (A) LENGTH: 47 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:53:

CTAATACGAC TCACTATAGG GCACGCGTGG TCGACGGCCC GGGCGGG                 47

(2) INFORMATION FOR SEQ ID NO:54:

(i) SEQUENCE CHARACTERISTICS:
        (A) LENGTH: 25 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:54:

CTAATACGAC TCACTATAGG GCGGG                                         25

(2) INFORMATION FOR SEQ ID NO:55:

(i) SEQUENCE CHARACTERISTICS:
        (A) LENGTH: 25 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:55:

CTAATACGAC TCACTATAGG GCGGG                                              25

(2) INFORMATION FOR SEQ ID NO:56:

(i) SEQUENCE CHARACTERISTICS:
        (A) LENGTH: 25 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:56:

CTAATACGAC TCACTATAGG GCGGG                                              25

(2) INFORMATION FOR SEQ ID NO:57:

(i) SEQUENCE CHARACTERISTICS:
        (A) LENGTH: 27 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:57:

CTAATACGAC TCACTATAGG GCGAGGG                                            27

(2) INFORMATION FOR SEQ ID NO:58:

(i) SEQUENCE CHARACTERISTICS:
        (A) LENGTH: 27 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:58:

CTAATACGAC TCACTATAGG GCGTGGG                                            27

(2) INFORMATION FOR SEQ ID NO:59:

(i) SEQUENCE CHARACTERISTICS:
        (A) LENGTH: 27 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:59:

CTAATACGAC TCACTATAGG GCGGAGG                                            27

(2) INFORMATION FOR SEQ ID NO:60:

(i) SEQUENCE CHARACTERISTICS:
        (A) LENGTH: 27 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:60:

CTAATACGAC TCACTATAGG GCGGTGG                                            27

(2) INFORMATION FOR SEQ ID NO:61:

(i) SEQUENCE CHARACTERISTICS:
        (A) LENGTH: 27 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:61:

CTAATACGAC TCACTATAGG GCGACGG                                              27

(2) INFORMATION FOR SEQ ID NO:62:

(i) SEQUENCE CHARACTERISTICS:
        (A) LENGTH: 27 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:62:

CTAATACGAC TCACTATAGG GCGATGG                                              27

(2) INFORMATION FOR SEQ ID NO:63:

(i) SEQUENCE CHARACTERISTICS:
        (A) LENGTH: 27 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:63:

CTAATACGAC TCACTATAGG GCGTTGG                                              27

(2) INFORMATION FOR SEQ ID NO:64:

(i) SEQUENCE CHARACTERISTICS:
        (A) LENGTH: 27 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:64:

CTAATACGAC TCACTATAGG GCGAGTG                                              27

(2) INFORMATION FOR SEQ ID NO:65:

(i) SEQUENCE CHARACTERISTICS:
        (A) LENGTH: 26 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:65:

TCCTAATACG ACTCACTATA GGAGGG                                               26

(2) INFORMATION FOR SEQ ID NO:66:

(i) SEQUENCE CHARACTERISTICS:
        (A) LENGTH: 27 bases (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:66:

CTAATACGAC TCACTATAGG GCGAGGG                                   27

(2) INFORMATION FOR SEQ ID NO:67:

(i) SEQUENCE CHARACTERISTICS:
            (A) LENGTH: 55 bases
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:67:

AAGCAGTGGT AACAACGCAG AGTACTTTTT TTTTTTTTTT TTTTTTTTTT TTTTT      55

(2) INFORMATION FOR SEQ ID NO:68:

(i) SEQUENCE CHARACTERISTICS:
            (A) LENGTH: 30 bases
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:68:

AAGCAGTGGT AACAACGCAG AGTACGCGGG                                30

(2) INFORMATION FOR SEQ ID NO:69:

(i) SEQUENCE CHARACTERISTICS:
            (A) LENGTH: 23 bases
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:69:

AAGCAGTGGT AACAACGCAG AGT                                       23

(2) INFORMATION FOR SEQ ID NO:70:

(i) SEQUENCE CHARACTERISTICS:
            (A) LENGTH: 21 bases
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:70:

TGTAGCGTGA AGACGACAGA A                                         21

(2) INFORMATION FOR SEQ ID NO:71:

(i) SEQUENCE CHARACTERISTICS:
            (A) LENGTH: 22 bases
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:71:

CTAATACGAC TCACTATAGG GC                                              22

(2) INFORMATION FOR SEQ ID NO:72:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:72:

TGCCATCCTA ATACGACTCA CTA                                             23

(2) INFORMATION FOR SEQ ID NO:73:

(i) SEQUENCE CHARACTERISTICS:
        (A) LENGTH: 22 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:73:

CTAATACGAC TCACGGATGG GC                                              22

(2) INFORMATION FOR SEQ ID NO:74:

(i) SEQUENCE CHARACTERISTICS:
        (A) LENGTH: 21 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:74:

TGATGCGAGT AGACGACAGA A                                               21

(2) INFORMATION FOR SEQ ID NO:75:

(i) SEQUENCE CHARACTERISTICS:
        (A) LENGTH: 21 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:75:

TGCTGCGAGA AGACGACAGA A                                               21

(2) INFORMATION FOR SEQ ID NO:76:

(i) SEQUENCE CHARACTERISTICS:
        (A) LENGTH: 21 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:76:

TTGCTGGCAG AAGACGACAG A                                               21

(2) INFORMATION FOR SEQ ID NO:77:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:77:

TACGATGCGA GTAGACGACA GAA        23

(2) INFORMATION FOR SEQ ID NO:78:

(i) SEQUENCE CHARACTERISTICS:
        (A) LENGTH: 22 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:78:

TGACCAGTGA GCAGAGTGAC GA        22

(2) INFORMATION FOR SEQ ID NO:79:

(i) SEQUENCE CHARACTERISTICS:
        (A) LENGTH: 27 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:79:

CCATCCAATT AACCCTCACT AAAGGGC        27

(2) INFORMATION FOR SEQ ID NO:80:

(i) SEQUENCE CHARACTERISTICS:
        (A) LENGTH: 21 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:80:

AAGCAGAGGC AACAACGCAG A        21

(2) INFORMATION FOR SEQ ID NO:81:

(i) SEQUENCE CHARACTERISTICS:
        (A) LENGTH: 22 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:81:

ACAAGACGAA GCACAAGAGG GC        22

(2) INFORMATION FOR SEQ ID NO:82:

(i) SEQUENCE CHARACTERISTICS:
        (A) LENGTH: 21 bases (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:82:

AAGCAGAGGC AACAACGCAG A                                               21

(2) INFORMATION FOR SEQ ID NO:83:

(i) SEQUENCE CHARACTERISTICS:
            (A) LENGTH: 19 bases
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:83:

TTCCGCTTGT CTGCTGGGC                                                  19

(2) INFORMATION FOR SEQ ID NO:84:

(i) SEQUENCE CHARACTERISTICS:
            (A) LENGTH: 17 bases
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:84:

CGTGCGGCCG CTTCGAG                                                    17

(2) INFORMATION FOR SEQ ID NO:85:

(i) SEQUENCE CHARACTERISTICS:
            (A) LENGTH: 15 bases
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:85:

GAGCGGCCGC ACGAG                                                      15

(2) INFORMATION FOR SEQ ID NO:86:

(i) SEQUENCE CHARACTERISTICS:
            (A) LENGTH: 25 bases
            (B) TYPE: nucleic acid
            (C) STRANDEDNESS: single
            (D) TOPOLOGY: linear (ii) MOLECULE TYPE: RNA (synthetic)

(xi) SEQUENCE DESCRIPTION: SEQ ID NO:86:

CTAATACGAC TCACTATAGG GCGGG                                           25

(2) INFORMATION FOR SEQ ID NO:87:

(i) SEQUENCE CHARACTERISTICS:
            (A) LENGTH: 29 bases
            (B) TYPE: nucleic acid
            (C) STRANDEDNESS: single
            (D) TOPOLOGY: linear (ii) MOLECULE TYPE: RNA (synthetic)

(xi) SEQUENCE DESCRIPTION: SEQ ID NO:87:

CTAATACGAC TCACTATAGG GCGGATGGG                                                29

(2) INFORMATION FOR SEQ ID NO:88:

(i) SEQUENCE CHARACTERISTICS:
            (A) LENGTH: 25 bases
            (B) TYPE: nucleic acid
            (C) STRANDEDNESS: single
            (D) TOPOLOGY: linear (ii) MOLECULE TYPE: RNA (synthetic)

(xi) SEQUENCE DESCRIPTION: SEQ ID NO:88:

CTAATACGAC TCACTATAGG GCNNN                                                    25

(2) INFORMATION FOR SEQ ID NO:89:

(i) SEQUENCE CHARACTERISTICS:
            (A) LENGTH: 25 bases
            (B) TYPE: nucleic acid
            (C) STRANDEDNESS: single
            (D) TOPOLOGY: linear (ii) MOLECULE TYPE: RNA (synthetic)

(xi) SEQUENCE DESCRIPTION: SEQ ID NO:89:

CTAATACGAC TCACTATAGG GCNNN                                                    25

(2) INFORMATION FOR SEQ ID NO:90:

(i) SEQUENCE CHARACTERISTICS:
            (A) LENGTH: 40 bases
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:90:

AAGCAGAGGC AACAACGCAG AGAGGGCAGC AGGCAGCGGG                                    40

(2) INFORMATION FOR SEQ ID NO:91:

(i) SEQUENCE CHARACTERISTICS:
            (A) LENGTH: 40 bases
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:91:

AGACGAAGCA CAAGAGGGCA CGAGCGGCCG CACGGCGGGG                                    40

(2) INFORMATION FOR SEQ ID NO:92:

(i) SEQUENCE CHARACTERISTICS:
            (A) LENGTH: 40 bases
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO:92:

ATACGACTCA CTATAGGGCT CGAGCGGCCG CACGGCGGGG                                    40

(2) INFORMATION FOR SEQ ID NO:93:

(i) SEQUENCE CHARACTERISTICS:
        (A) LENGTH: 32 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:93:

AAGCAGAGTG CTAACAACGC AGAGTACGCG GG     32

(2) INFORMATION FOR SEQ ID NO:94:

(i) SEQUENCE CHARACTERISTICS:
        (A) LENGTH: 22 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:94:

ATACGACTCA CTATAGGGCG GG     22

(2) INFORMATION FOR SEQ ID NO:95:

(i) SEQUENCE CHARACTERISTICS:
        (A) LENGTH: 24 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:95:

ATACGACTCA CTATAGGGCG CGGG     24

(2) INFORMATION FOR SEQ ID NO:96:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:96:

ATTAACCCTC ACTAAAGGGC GGG     23

(2) INFORMATION FOR SEQ ID NO:97:

(i) SEQUENCE CHARACTERISTICS:
        (A) LENGTH: 41 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:97:

ATTAACCCTC ACTAAAGGGC TCGAGCGGCC GCACGGCGGG G     41

(2) INFORMATION FOR SEQ ID NO:98:

(i) SEQUENCE CHARACTERISTICS:
        (A) LENGTH: 30 bases (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:98:

AAGCAGTGGT ATCAACGCAG AGTACGCGGG                                          30

(2) INFORMATION FOR SEQ ID NO:99:

(i) SEQUENCE CHARACTERISTICS:
        (A) LENGTH: 28 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:99:

AAGCAGTGGT AACAACGCAG AGTGCGGG                                            28

(2) INFORMATION FOR SEQ ID NO:100:

(i) SEQUENCE CHARACTERISTICS:
        (A) LENGTH: 40 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:100:

AAGCAGTGGT AACAACGCAG AGTGGGCAGC AGGCAGCGGG                               40

(2) INFORMATION FOR SEQ ID NO:101:

(i) SEQUENCE CHARACTERISTICS:
        (A) LENGTH: 30 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:101:

AAGCAGTGGT ATCAACGCAG AGTACGCGGG                                          30

(2) INFORMATION FOR SEQ ID NO:102:

(i) SEQUENCE CHARACTERISTICS:
        (A) LENGTH: 30 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:102:

AAGCAGTGGT AACAACGCAG AGTACGCGGG                                          30

(2) INFORMATION FOR SEQ ID NO:103:

(i) SEQUENCE CHARACTERISTICS:
        (A) LENGTH: 40 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:103:

AAGCAGTGGT AACAACGCAG AGTGGGCAGC AGCCAGCGGG                40

(2) INFORMATION FOR SEQ ID NO:104:

(i) SEQUENCE CHARACTERISTICS:
      (A) LENGTH: 40 bases
      (B) TYPE: nucleic acid
      (C) STRANDEDNESS: single
      (D) TOPOLOGY: linear (ii) MOLECULE TYPE: DNA (synthetic)

(xi) SEQUENCE DESCRIPTION: SEQ ID NO:104:

ATACGACTCA CTATAGGGCT CGAGCGGCCG CACGGCGGGG                40

(2) INFORMATION FOR SEQ ID NO:105:

(i) SEQUENCE CHARACTERISTICS:
      (A) LENGTH: 42 bases
      (B) TYPE: nucleic acid
      (C) STRANDEDNESS: single
      (D) TOPOLOGY: linear (ii) MOLECULE TYPE: DNA (synthetic)

(xi) SEQUENCE DESCRIPTION: SEQ ID NO:105:

ATACGACTCA CTATAGGGCT CGAGCGGCCG CCCGGGCAGG GG                42

(2) INFORMATION FOR SEQ ID NO:106:

(i) SEQUENCE CHARACTERISTICS:
      (A) LENGTH: 42 bases
      (B) TYPE: nucleic acid
      (C) STRANDEDNESS: single
      (D) TOPOLOGY: linear (ii) MOLECULE TYPE: DNA (synthetic)

(xi) SEQUENCE DESCRIPTION: SEQ ID NO:106:

ATACGACTCA CTATAGGGCT CGGTCGGGCA GGCACGGCGG GG                42

(2) INFORMATION FOR SEQ ID NO:107:

(i) SEQUENCE CHARACTERISTICS:
      (A) LENGTH: 40 bases
      (B) TYPE: nucleic acid
      (C) STRANDEDNESS: single
      (D) TOPOLOGY: linear (ii) MOLECULE TYPE: DNA (synthetic)

(xi) SEQUENCE DESCRIPTION: SEQ ID NO:107:

TTCCGCTTGT CTGCTGGGCT CGTGCGGCCG CTCGGCGGGG                40

(2) INFORMATION FOR SEQ ID NO:108:

(i) SEQUENCE CHARACTERISTICS:
      (A) LENGTH: 40 bases
      (B) TYPE: nucleic acid
      (C) STRANDEDNESS: single
      (D) TOPOLOGY: linear (ii) MOLECULE TYPE: DNA (synthetic)

(xi) SEQUENCE DESCRIPTION: SEQ ID NO:108:

AGACGAAGCA CAAGAGGGCA CGAGCAGCGG CACGGCGGGG                40

(2) INFORMATION FOR SEQ ID NO:109:

(i) SEQUENCE CHARACTERISTICS:
        (A) LENGTH: 58 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:109:

TGACCAGTGA GCAGAGTGAC GAGTACTTTT TTTTTTTTTT TTTTTTTTTT TTTTTTVN      58

(2) INFORMATION FOR SEQ ID NO:110:

(i) SEQUENCE CHARACTERISTICS:
        (A) LENGTH: 59 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:110:

CCATCCTAAT ACGACTCACT ATAGGGCTTT TTTTTTTTTT TTTTTTTTTT TTTTTTTVN      59

(2) INFORMATION FOR SEQ ID NO:111:

(i) SEQUENCE CHARACTERISTICS:
        (A) LENGTH: 52 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:111:

AATACGACTC ACTATAGGGC TTTTTTTTTT TTTTTTTTTT TTTTTTTTTT VN      52

(2) INFORMATION FOR SEQ ID NO:112:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:112:

TGCTGCGGAA GACGACAGAA GGG      23

(2) INFORMATION FOR SEQ ID NO:113:

(i) SEQUENCE CHARACTERISTICS:
        (A) LENGTH: 20 bases
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:113:

TGCTGCGGAA GACGACAGAA      20

(2) INFORMATION FOR SEQ ID NO:114:

(i) SEQUENCE CHARACTERISTICS:
        (A) LENGTH: 47 bases

```
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:114:

AATTCGAGCG GCCGCTTTTT TTTTTTTTTT TTTTTTTTTT TTTTTVN                    47
```